(12) United States Patent
Okawa

(10) Patent No.: US 7,989,581 B2
(45) Date of Patent: Aug. 2, 2011

(54) POLYETHER FROM RING-OPENING OF GLYCIDYL ETHER WITH (C2-C5 ALKYLENE OXIDE) MONOHYDRIC ALCOHOL

(75) Inventor: Tadashi Okawa, Ichihara (JP)

(73) Assignee: Dow Corning Toray Company, Ltd., Chiyoda-Ku, Tokyo (JP)

( * ) Notice: Subject to any disclaimer, the term of this patent is extended or adjusted under 35 U.S.C. 154(b) by 145 days.

(21) Appl. No.: 12/301,600

(22) PCT Filed: May 17, 2007

(86) PCT No.: PCT/JP2007/000530
§ 371 (c)(1), (2), (4) Date: May 7, 2009

(87) PCT Pub. No.: WO2007/135770
PCT Pub. Date: Nov. 29, 2007

(65) Prior Publication Data
US 2010/0022732 A1  Jan. 28, 2010

(30) Foreign Application Priority Data
May 19, 2006 (JP) .................................. 2006-139827

(51) Int. Cl.
C08G 65/28 (2006.01)
C08L 71/08 (2006.01)
(52) U.S. Cl. ........................................ 528/405; 525/404
(58) Field of Classification Search .................. 525/404; 528/405
See application file for complete search history.

(56) References Cited

U.S. PATENT DOCUMENTS

| | | | |
|---|---|---|---|
| 4,025,548 A | 5/1977 | Huemmer et al. | |
| 4,722,978 A | 2/1988 | Yu | |
| 2007/0049687 A1 * | 3/2007 | Hashimoto et al. | 524/700 |

FOREIGN PATENT DOCUMENTS

| | | |
|---|---|---|
| JP | 50137914 A | 11/1975 |
| JP | 56043323 A | 4/1981 |
| JP | 62059236 A | 3/1987 |
| JP | 63227630 A | 9/1988 |
| JP | 3503168 A | 7/1991 |
| JP | 06087931 A | 3/1994 |
| JP | 80239467 A | 9/1996 |
| JP | 2672385 A | 11/1997 |
| JP | 2001342156 A | 11/2001 |
| JP | 2002179788 A | 6/2002 |
| JP | 2002533495 A | 10/2002 |
| JP | 2003002964 A | 1/2003 |
| JP | 2005272733 A | 10/2005 |
| JP | 2005350613 A | 12/2005 |
| WO | WO 8912618 A1 | 12/1989 |

OTHER PUBLICATIONS

Chemical Book, lauryl glycidyl ether, 2010, one page.*
English language abstract for JP50137914 extracted from espacenet.com database, dated May 11, 2009.
English language abstract for JP56043323 extracted from espacenet.com database, dated May 11, 2009.
English language abstract for JP 63227630 extracted from espacenet.com database, dated May 11, 2009.
English language abstract for JP 3503168 extracted from espacenet.com database, dated May 11, 2009.
English language translation and abstract for JP 06087931 extracted from PAJ database, dated May 11, 2009, 32 pages.
English language translation and abstract for JP 08239467 extracted from PAJ database, dated May 11, 2009, 44 pages.
English language abstract for JP 2672385 extracted from espacenet.com database, dated May 11, 2009.
English language translation and abstract for JP 2001342156 extracted from PAJ database, dated May 11, 2009, 54 pages.
English language translation and abstract for JP 2002179788 extracted from PAJ database, dated May 11, 2009, 31 pages.
English language translation and abstract for JP 2002533495 extracted from espacenet.com and PAJ database, dated May 11, 2009, 32 pages.
English language translation and abstract for JP 2003002964 extracted from PAJ database, dated May 11, 2009, 31 pages.
English language translation and abstract for JP 2005272733 extracted from PAJ database, dated May 11, 2009, 84 pages.
English language translation and abstract for JP 2005350613 extracted from PAJ database, dated May 11, 2009, 47 pages.

* cited by examiner

Primary Examiner — Robert Sellers
(74) Attorney, Agent, or Firm — Howard & Howard Attorneys PLLC

(57) ABSTRACT

Polyether represented by $R(-O-X_n-Z_m-Y)_p$ {R is a monovalent hydrocarbyl group that contains no more than 20 carbon atoms and that may contain an aliphatically unsaturated bond or is a group comprising the preceding group having an ether linkage therein; n is 1 to 200; m is 0 to 200; $0<n/(n+m) \leq 1$; X is a group provided by the ring-opening polymerization of a glycidyl ether; Z is an alkyleneoxy group having 2 to 6 carbon atoms; p is 1 to 6; Y is H or is a monovalent hydrocarbyl group, acyl group that contains no more than 20 carbon atoms and that may contain an aliphatically unsaturated bond or glycidyl group; and the configuration of the X and Z groups may be, inter alia, random} wherein either R or Y contains or both R and Y contain an aliphatically unsaturated bond and the molecular weight distribution (polydispersity) determined versus a polystyrene standard is 1.25 to 1.00. A method of production in which base catalyst-mediated ring-opening polymerization is carried out on glycidyl ether or glycidyl ether and an alkylene oxide having 2 to 6 carbon atoms in the presence of a monohydric to hexahydric alcohol.

8 Claims, No Drawings

POLYETHER FROM RING-OPENING OF GLYCIDYL ETHER WITH (C2-C5 ALKYLENE OXIDE) MONOHYDRIC ALCOHOL

RELATED APPLICATIONS

This application claims priority to and all the advantages of International Patent Application No. PCT/JP 2007/00530, filed on May 17, 2007, which claims priority to Japanese Patent Application No. JP2006-139827 filed on May 19, 2006.

TECHNICAL FIELD

The present invention relates to novel polyethers that are homopolymers of a glycidyl ether or copolymers of a glycidyl ether and an alkylene oxide having 2 to 6 carbon atoms that have an aliphatically unsaturated bond in a terminal group or linking group and particularly that have a terminal double bond. The present invention further relates to methods of producing these novel polyethers.

BACKGROUND ART

Polyethers having an aliphatic double bond in molecular chain terminal position, that is, double bond-terminated polyethers, are compounds useful, inter alia, as reactive surfactants for emulsion polymerization, as intermediates for such reactive surfactants, and as intermediates for polysiloxane/polyether copolymers. Japanese Patent No. 2,672,385 (JP 2,672,385 B) discloses a method of producing a polyether having the allyloxy group at one terminal by the addition polymerization of butylene oxide and ethylene oxide on allyl alcohol in the presence of a base catalyst. Japanese Unexamined Patent Application Publication No. 2001-342156 (JP 2001-342156 A) discloses a method of producing an unsaturated aliphatic alcohol/alkylene oxide adduct by the addition polymerization of an alkylene oxide on an unsaturated aliphatic alcohol in the presence of the strong acid salt of a metal. JP 2002-179788 A discloses a method of producing a polyether that has an alkenyl at one terminal and hydroxyl at the other terminal; this method proceeds by the addition polymerization of an alkylene oxide on an unsaturated aliphatic alcohol in the presence of a Lewis acid catalyst or composite metal oxide catalyst. However, the structural unit of these polyethers is limited to the alkyleneoxy group.

JP S62-059236 A discloses a method of producing a polyether having an aliphatic double bond at one molecular chain terminal and hydroxyl group at the other terminal; this method proceeds through the ring-opening polymerization of an alkylene oxide or a glycidyl ether or both in the presence of an aliphatic double bond-containing alcohol and a cationic initiator (for example, a Friedel-Crafts catalyst, protonic acid). JP S62-059236 A also discloses the polyether produced by this method, i.e., polyether having an aliphatic double bond at one molecular chain terminal and hydroxyl group at the other terminal. However, due to secondary reactions that accompany this polymerization, the molecular weight distribution has a broad polydispersity of at least 1.3 to a maximum of 7.5, and only a low-purity polyether is obtained. Low-purity alkenyl-monoterminated polyether with such a broad molecular weight distribution (polydispersity) is unsuitable as a reactive surfactant for emulsion polymerization and is also unsuitable as an intermediate in the production of polyether-modified organopolysiloxanes using the hydrosilylation reaction. It is also unsuitable as an intermediate in the production of block copolymers. Moreover, a polyether having alkenyl at only one terminal is unsuitable as an intermediate for the production of block copolymers. In addition, the oxidation resistance is unsatisfactory when the alkyleneoxy group is the main structural unit.

[Patent Reference 1] JP 2,672,385 B
[Patent Reference 2] JP 2001-342156 A
[Patent Reference 3] JP 2002-179788 A
[Patent Reference 4] JP S62-059236 A

DISCLOSURE OF THE INVENTION

Problems to Be Solved By the Invention

The present inventors therefore carried out concerted research in order to develop a polyether that would be free of the problems cited above and achieved this invention as a result. A problem to be addressed by the present invention is the introduction of a novel polyether that is either a straight-chain homopolymer obtained by the ring-opening addition polymerization of a glycidyl ether on a monohydric alcohol or a straight-chain copolymer obtained by the ring-opening addition copolymerization of a glycidyl ether and an alkylene oxide having 2 to 5 carbon atoms on a monohydric alcohol, that has an aliphatically unsaturated bond in a molecular chain terminal group and in particular that has a terminal double bond, and that has a narrow molecular weight distribution (polydispersity). Another problem to be addressed by the present invention is the introduction of a polyether that exhibits an excellent oxidation resistance in addition to being equipped with the aforementioned characteristic features.

Another problem to be addressed by the present invention is the introduction of a novel polyether that is either a straight-chain or branched homopolymer obtained by the ring-opening addition polymerization of a glycidyl ether on a dihydric to hexahydric alcohol or a straight-chain or branched copolymer obtained by the ring-opening addition polymerization of a glycidyl ether and an alkylene oxide having 2 to 6 carbon atoms on a dihydric to hexahydric alcohol, that has an aliphatically unsaturated bond in a molecular chain terminal group or in a linking group and in particular that has a terminal double bond, and that has a narrow molecular weight distribution (polydispersity).

Another problem to be addressed by the present invention is the introduction of a polyether that exhibits an excellent oxidation resistance in addition to being equipped with the aforementioned characteristic features. A further problem to be addressed by the present invention is the introduction of methods that can produce precisely the aforementioned polyethers in good purities.

Means Solving the Problems

The inventions in the first group of inventions of this application relate to the following.

[1] A polyether represented by general formula (1)

$$R-O-X_n-Z_m-Y \tag{1}$$

{in the formula, R is a monovalent hydrocarbyl group that contains no more than 20 carbon atoms and that may contain an aliphatically unsaturated bond or a group comprising said monovalent hydrocarbyl group having an ether linkage (C—O—C) therein;

n is 1 to 200; m is 0 to 200; $0 < n/(n+m) \leq 1$;

Z is an alkyleneoxy group having 2 to 6 carbon atoms;

Y is hydrogen atom or is a group selected from the group consisting of a monovalent hydrocarbyl group that contains no more than 20 carbon atoms and that may contain an aliphatically unsaturated bond, an acyl group that contains no more than 20 carbon atoms and that may contain an aliphatically unsaturated bond, and glycidyl group; and X is a group represented by general formula (2) or general formula (3)

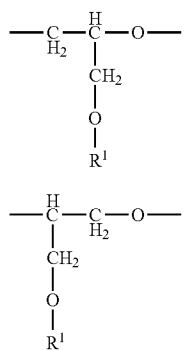

(in the preceding formulas, $R^1$ is a monovalent hydrocarbyl group or monovalent fluorohydrocarbyl group); wherein the configuration of the X and Z groups may be random, alternating, block, or a combination of the preceding}, wherein either R or Y contains or both R and Y contain an aliphatically unsaturated bond and the molecular weight distribution (polydispersity) determined versus a polystyrene standard is 1.25 to 1.00.

[1-1] The polyether according to [1], wherein the n in $—X_n—$ is 2 to 200; $X_n$ is a homopolymer, random copolymer, or block copolymer; the m in $—Z_m 13$ is 2 to 200; and $Z_m$ is a homopolymer, random copolymer, or block copolymer.

[2] The polyether according to [1], wherein R is a double bond-terminated monovalent hydrocarbyl group having 2 to 20 carbon atoms or a group comprising said monovalent hydrocarbyl group having an ether linkage (C—O—C) therein and Y is hydrogen atom.

[3] The polyether according to [1], wherein R is a double bond-terminated monovalent hydrocarbyl group having 2 to 20 carbon atoms or a group comprising said monovalent hydrocarbyl group having an ether linkage (C—O—C) therein, and Y is a group selected from the group consisting of an aliphatically unsaturated bond-free monovalent hydrocarbyl group that contains no more than 20 carbon atoms, an aliphatically unsaturated bond-free acyl group that contains no more than 20 carbon atoms, and glycidyl group.

[4] The polyether according to [1], wherein R is an aliphatically unsaturated bond-free monovalent hydrocarbyl group that contains no more than 20 carbon atoms or a group comprising said monovalent hydrocarbyl group having an ether linkage (C—O—C) therein, and Y is a double bond-terminated monovalent hydrocarbyl group having 2 to 20 carbon atoms or a double bond-terminated acyl group having 2 to 20 carbon atoms.

[5] The polyether according to [1], wherein R is a double bond-terminated monovalent hydrocarbyl group having 2 to 20 carbon atoms or is a group comprising said monovalent hydrocarbyl group having an ether linkage (C—O—C) therein, and Y is a double bond-terminated monovalent hydrocarbyl group having 2 to 20 carbon atoms or a double bond-terminated acyl group having 2 to 20 carbon atoms.

[6] The polyether according to any of [2] to [5], wherein $R^1$ is an aliphatically unsaturated bond-free monovalent hydrocarbyl group.

[7] The polyether according to any of [2] to [6], wherein the double bond-terminated monovalent hydrocarbyl group having 2 to 20 carbon atoms constituting R or Y is a group selected from the group consisting of alkenyl, alkenylphenyl, and alkenylaralkyl; the group comprising said monovalent hydrocarbyl group having an ether linkage (C—O—C) therein is alkenyloxyalkyl or alkenyloxyphenyl; the aliphatically unsaturated bond-free monovalent hydrocarbyl group having no more than 20 carbon atoms constituting R or Y is a group selected from the group consisting of alkyl, phenyl, alkylphenyl, aralkyl, and alkylaralkyl; the group comprising said monovalent hydrocarbyl group having an ether linkage (C—O—C) therein is alkyloxyalkyl or alkyloxyphenyl; and the aliphatically unsaturated bond-free monovalent hydrocarbyl group constituting $R^1$ is a group selected from the group consisting of alkyl, phenyl, and alkylphenyl.

[8] The polyether according to [7], wherein the alkyl constituting R is a group selected from the group consisting of methyl, ethyl, propyl, butyl, pentyl, hexyl, and an alkyl having 7 to 10 carbon atoms; the alkylphenyl constituting R is a group selected from the group consisting of tolyl, xylyl, and ethylphenyl; the alkenyl constituting R is a group selected from the group consisting of allyl, methallyl, 3-butenyl, 1,1-dimethyl-2-propenyl, i.e., the group represented by the formula

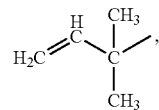

4-pentenyl, 5-hexenyl, 10-undecenyl, and isoprenyl; the alkenylphenyl is vinylphenyl or allylphenyl; the alkenylaralkyl is vinylbenzyl; the alkenyloxyalkyl is allyloxyethyl; the alkenyloxyphenyl is allyloxyphenyl; the alkyl constituting $R^1$ is a group selected from the group consisting of methyl, ethyl, propyl, and butyl; the alkyl constituting Y is a group selected from the group consisting of methyl, ethyl, propyl, butyl, pentyl, hexyl, and an alkyl having 7 to 20 carbon atoms; the alkenyl constituting Y is a group selected from the group consisting of allyl, methallyl, 3-butenyl, 1,1-dimethyl-2-propenyl, i.e., the group represented by the formula

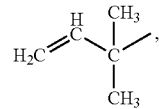

5-hexenyl, 10-undecenyl, and isoprenyl; the double bond-terminated acyl group having 2 to 20 carbon atoms constituting Y is a group selected from the group consisting of acryl, methacryl, crotonyl, and undecenoyl; and the aliphatically unsaturated bond-free acyl group having no more than 20 carbon atoms constituting Y is a group selected from the group consisting of acetyl, propionyl, butanoyl, pentanoyl, hexanoyl, heptanoyl, octanoyl, decanoyl, dodecanoyl, tridecanoyl, tetradecanoyl, hexadecanoyl, and octadecanoyl.

[9] The polyether according to any of [1] to [8], wherein $0.5<n/(n+m)\leq 1$.

[10] The polyether according to [9], wherein $0.9<n/(n+m)\leq 1$.

The inventions in the second group of inventions of this application relate to the following.

[11] A polyether represented by general formula (4)

$$R^2(-O-X_n-Z_m-Y)_p \quad (4)$$

{in the formula, $R^2$ is a p-valent hydrocarbyl group that contains no more than 20 carbon atoms and that may contain an aliphatically unsaturated bond or a group comprising said p-valent hydrocarbyl group having an ether linkage (C—O—C) therein;

n is 1 to 200; m is 0 to 200; $0<n/(n+m)\leq 1$;

Z is an alkyleneoxy group having 2 to 6 carbon atoms;

p is an integer with a value of 2 to 6;

Y is hydrogen atom or is a group selected from the group consisting of a monovalent hydrocarbyl group that contains no more than 20 carbon atoms and that may contain an aliphatically unsaturated bond, an acyl group that contains no more than 20 carbon atoms and that may contain an aliphatically unsaturated bond, and glycidyl group; and X is a group represented by general formula (2) or general formula (3)

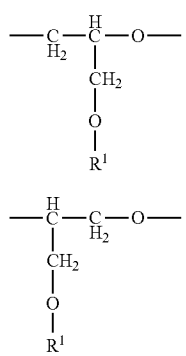

(in the preceding formulas, $R^1$ is a monovalent hydrocarbyl group or monovalent fluorohydrocarbyl group);

wherein the configuration of the X and Z groups may be random, alternating, block, or a combination of the preceding}, wherein either $R^2$ or Y contains or both $R^2$ and Y contain an aliphatically unsaturated bond and the molecular weight distribution (polydispersity) determined versus a polystyrene standard is 1.25 to 1.00.

[11-1] The polyether according to [1], wherein the n in —$X_n$— is 2 to 200; $X_n$ is a homopolymer, random copolymer, or block copolymer; the m in —$Z_m$— is 2 to 200; and $Z_m$ is a homopolymer, random copolymer, or block copolymer.

[12] The polyether according to [11], wherein $R^2$ is a double bond-terminated divalent to hexavalent hydrocarbyl group having 2 to 20 carbon atoms or a group comprising said divalent to hexavalent hydrocarbyl group having an ether linkage (C—O—C) therein, and Y is hydrogen atom or is a group selected from the group consisting of an aliphatically unsaturated bond-free monovalent hydrocarbyl group having no more than 20 carbon atoms, an aliphatically unsaturated bond-free acyl group having no more than 20 carbon atoms, and a glycidyl group.

[13] The polyether according to [12], wherein $R^1$ is an aliphatically unsaturated bond-free monovalent hydrocarbyl group.

[14] The polyether according to [12] or [13], wherein the double bond-terminated divalent to hexavalent hydrocarbyl group having 2 to 20 carbon atoms constituting $R^2$ is a double bond-terminated divalent to hexavalent aliphatic hydrocarbyl group; the group comprising said divalent to hexavalent aliphatic hydrocarbyl group having an ether linkage (C—O—C) therein is a group comprising allyloxy group-containing divalent to hexavalent aliphatic hydrocarbyl group having an ether linkage (C—O—C) therein; the aliphatically unsaturated bond-free monovalent hydrocarbyl group constituting $R^1$ is a group selected from the group consisting of alkyl, phenyl, and alkylphenyl; the aliphatically unsaturated bond-free monovalent hydrocarbyl group having no more than 20 carbon atoms constituting Y is a group selected from the group consisting of alkyl, phenyl, and alkylphenyl; and the aliphatically unsaturated bond-free acyl group having no more than 20 carbon atoms is a saturated aliphatic acyl.

[15] The polyether according to [14], wherein the allyloxy group-containing divalent to hexavalent aliphatic hydrocarbyl group or a group comprising said allyloxy group-containing divalent to hexavalent aliphatic hydrocarbyl group having an ether linkage (C—O—C) therein is a group having any of the following structural formulas

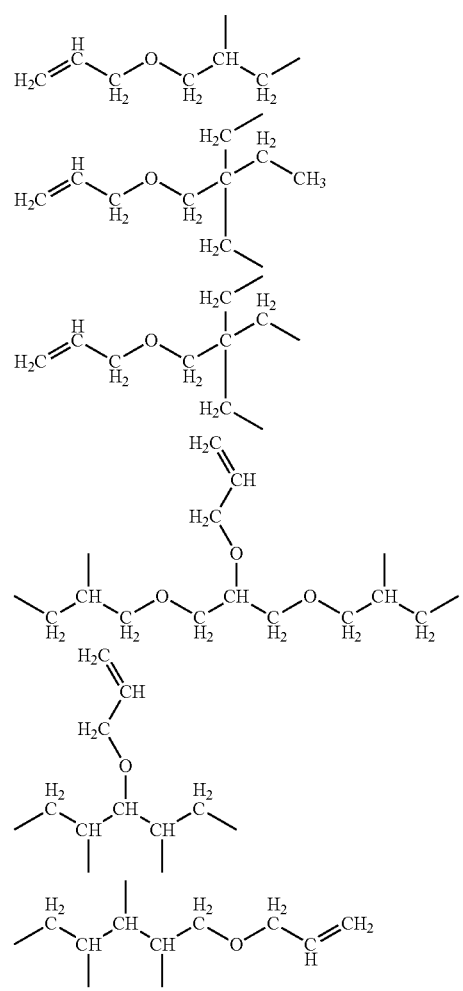

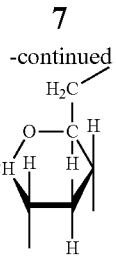

and the alkyl constituting $R^1$ is a group selected from the group consisting of methyl, ethyl, propyl, and butyl.

[16] The polyether according to [11], wherein $R^2$ is an aliphatically unsaturated bond-free divalent to hexavalent hydrocarbyl group having no more than 20 carbon atoms or a group comprising said divalent to hexavalent hydrocarbyl group having an ether linkage (C—O—C) therein, and Y is a double bond-terminated monovalent hydrocarbyl group having 2 to 20 carbon atoms or a double bond-terminated Acyl group having 2 to 20 carbon atoms.

[17] The polyether according to [16], wherein $R^1$ is an aliphatically unsaturated bond-free monovalent hydrocarbyl group.

[18] The polyether according to [17], wherein the aliphatically unsaturated bond-free divalent to hexavalent hydrocarbyl group having no more than 20 carbon atoms constituting $R^2$ is a divalent to hexavalent saturated aliphatic hydrocarbyl; the group comprising said divalent to hexavalent saturated aliphatic hydrocarbyl group having an ether linkage (C—O—C) therein is an alkyleneoxyalkylene group; the aliphatically unsaturated bond-free monovalent hydrocarbyl group constituting $R^1$ is a group selected from the group consisting of alkyl, phenyl, and alkylphenyl; the double bond-terminated monovalent hydrocarbyl group having 2 to 20 carbon atoms constituting Y is alkenyl; and the double bond-terminated acyl group having 2 to 20 carbon atoms is unsaturated aliphatic acyl.

[19] The polyether according to [18], wherein the divalent aliphatic hydrocarbyl constituting $R^2$ is any selection from ethylene to hexylene; the alkyleneoxyalkylene constituting $R^2$ is ethyleneoxyethylene or propyleneoxypropylene; the alkyl constituting $R^1$ is a group selected from the group consisting of methyl, ethyl, propyl, and butyl; the alkenyl constituting Y is allyl or methallyl; and the double bond-terminated unsaturated aliphatic acyl group constituting Y is a group selected from the group consisting of acryl, methacryl, crotonyl, and undecenyl.

[20] The polyether according to any of [11] to [19], wherein $0.5<n/(n+m)\leq 1$.

[21] The polyether according to [20], wherein $0.9<n/(n+m)\leq 1$.

The inventions in the third group of inventions of this application relate to the following.

[22] A method of producing a polyether represented by general formula (1)

{in the formula, R is a double bond-terminated monovalent hydrocarbyl group having 2 to 20 carbon atoms or a group comprising said monovalent hydrocarbyl group having an ether linkage (C—O—C) therein;
n is 1 to 200; m is 0 to 200; $0<n/(n+m)\leq 1$;
X is a group represented by the above-cited general formula (2) or (3);
Z is an alkyleneoxy group having 2 to 6 carbon atoms;
Y is a group selected from the group consisting of an aliphatically unsaturated bond-free monovalent hydrocarbyl group having no more than 20 carbon atoms, an aliphatically unsaturated bond-free acyl group having no more than 20 carbon atoms, and a glycidyl group; and
the configuration of the X and Z groups may be random, alternating, block, or a combination of the preceding} defined in [2],
wherein the molecular weight distribution (polydispersity) determined versus a polystyrene standard is 1.25 to 1.00, comprising
(1) carrying out a ring-opening polymerization or a ring-opening copolymerization, in the presence of a base catalyst and a monohydric alcohol with general formula (5)

(in the formula, R is a double bond-terminated monovalent hydrocarbyl group having 2 to 20 carbon atoms or a group comprising said monovalent hydrocarbyl group having an ether linkage (C—O—C) therein),
of only a glycidyl ether represented by general formula (6) or of this glycidyl ether and an alkylene oxide

($R^1$ in the formula is a monovalent hydrocarbyl group or a monovalent fluorohydrocarbyl group); and
(2) thereafter stopping the polymerization by the addition of an acid.

[23] A method of producing a polyether represented by general formula (1)

{in the formula, R is a double bond-terminated monovalent hydrocarbyl group having 2 to 20 carbon atoms or a group comprising said monovalent hydrocarbyl group having an ether linkage (C—O—C) therein;
n is 1 to 200; m is 0 to 200; $0<n/(n+m)\leq 1$;
X is a group represented by the above-cited general formula (2) or (3);
Z is an alkyleneoxy group having 2 to 6 carbon atoms;
Y is a group selected from the group consisting of an aliphatically unsaturated bond-free monovalent hydrocarbyl group that contains no more than 20 carbon atoms, an aliphatically unsaturated bond-free acyl group that contains no more than 20 carbon atoms, and glycidyl group; and
the configuration of the X and Z groups may be random, alternating, block, or a combination of the preceding} defined in [3],
wherein the molecular weight distribution (polydispersity) determined versus a polystyrene standard is 1.25 to 1.00, comprising
(1) carrying out a ring-opening polymerization or a ring-opening copolymerization, in the presence of a base catalyst and a monohydric alcohol with general formula (5)

(in the formula, R is a double bond-terminated monovalent hydrocarbyl group having 2 to 20 carbon atoms or a group comprising said monovalent hydrocarbyl group having an ether linkage (C—O—C) therein), of only the glycidyl ether represented by the aforementioned general formula (6) or of this glycidyl ether and an alkylene oxide having 2 to 6 carbon atoms;
(2) replacing the H of the terminal hydroxyl group with an alkali metal by reacting the polymerization product with an alkali metal hydroxide; and
(3) then carrying out a reaction with an aliphatically unsaturated bond-free hydrocarbyl monohalide having no more than 20 carbon atoms, aliphatically unsaturated bond-free acyl monohalide having no more than 20 carbon atoms, or epichlorohydrin.

[24] A method of producing a polyether represented by general formula (1)

$$R\text{—}O\text{—}X_n\text{—}Z_m\text{—}Y \tag{1}$$

{in the formula, R is an aliphatically unsaturated bond-free monovalent hydrocarbyl group having no more than 20 carbon atoms or a group comprising said monovalent hydrocarbyl group having an ether linkage (C—O—C) therein; n is 1 to 200; m is 0 to 200; 0<n/(n+m)≦1;
X is a group represented by the above-cited general formula (2) or (3);
Z is an alkyleneoxy group having 2 to 6 carbon atoms;
Y is a group selected from the group consisting of a double bond-terminated monovalent hydrocarbyl group having 2 to 20 carbon atoms, a double bond-terminated acyl group having 2 to 20 carbon atoms, and glycidyl group; and
the configuration of the X and Z groups may be random, alternating, block, or a combination of the preceding} defined in [4],
wherein the molecular weight distribution (polydispersity) determined versus a polystyrene standard is 1.25 to 1.00, comprising
(1) carrying out a ring-opening polymerization or a ring-opening copolymerization, in the presence of a base catalyst and a monohydric alcohol with general formula (5)

$$ROH \tag{5}$$

(in the formula, R is an aliphatically unsaturated bond-free monovalent hydrocarbyl group having no more than 20 carbon atoms or a group comprising said monovalent hydrocarbyl group having an ether linkage (C—O—C) therein),
of only the glycidyl ether represented by the aforementioned general formula (6) or of this glycidyl ether and an alkylene oxide having 2 to 6 carbon atoms;
(2) replacing the H of the terminal hydroxyl group with an alkali metal by reacting the polymerization product with an alkali metal hydroxide; and
(3) then carrying out a reaction with a double bond-terminated hydrocarbyl monohalide or a double bond-terminated acyl monohalide having 2 to 20 carbon atoms.

[25] A method of producing a polyether represented by general formula (1)

$$R\text{—}O\text{—}X_n\text{—}Z_m\text{—}Y \tag{1}$$

{in the formula, R is a double bond-terminated monovalent hydrocarbyl group having 2 to 20 carbon atoms or a group comprising said monovalent hydrocarbyl group having an ether linkage (C—O—C) therein;
X, Z, n, and m are as described in [1]; and
Y is a double bond-terminated monovalent hydrocarbyl group having 2 to 20 carbon atoms or a double bond-terminated acyl group having 2 to 20 carbon atoms} defined in [5], wherein the molecular weight distribution (polydispersity) determined versus a polystyrene standard is 1.25 to 1.00, comprising
(1) carrying out a ring-opening polymerization or a ring-opening copolymerization, in the presence of a base catalyst and a monohydric alcohol with general formula (5)

$$ROH \tag{5}$$

(in the formula, R is a double bond-terminated monovalent hydrocarbyl group having 2 to 20 carbon atoms or a group comprising said monovalent hydrocarbyl group having an ether linkage (C—O—C) therein),
of only the glycidyl ether represented by the aforementioned general formula (6) or of this glycidyl ether and an alkylene oxide having 2 to 6 carbon atoms;
(2) replacing the H of the terminal hydroxyl group with an alkali metal by reacting the polymerization product with an alkali metal hydroxide; and
(3) then carrying out a reaction with a double bond-terminated hydrocarbyl monohalide having 2 to 20 carbon atoms or a double bond-terminated acyl monohalide having 2 to 20 carbon atoms.

The inventions in the fourth group of inventions of this application relate to the following.

[26] A method of producing a polyether represented by general formula (4)

$$R^2(\text{—}O\text{—}X_n\text{—}Z_m\text{—}Y)_p \tag{4}$$

{in the formula, $R^2$ is a double bond-terminated p-valent hydrocarbyl group having 2 to 20 carbon atoms or a group comprising said p-valent hydrocarbyl group having an ether linkage (C—O—C) therein;
n is 1 to 200; m is 0 to 200; 0<n/(n+m)≦1;
Z is an alkyleneoxy group having 2 to 6 carbon atoms;
p is an integer with a value of 2 to 6;
Y is hydrogen atom;
X is a group represented by the aforementioned general formula (2) or general formula (3); and
the configuration of the X and Z groups may be random, alternating, block, or a combination of the preceding} defined in [12],
wherein the molecular weight distribution (polydispersity) determined versus a polystyrene standard is 1.25 to 1.00, comprising
(1) carrying out a ring-opening polymerization or a ring-opening copolymerization, in the presence of a base catalyst and a p-hydric alcohol with general formula (7)

$$R^2(OH)_p \tag{7}$$

(in the formula, $R^2$ is a double bond-terminated p-valent hydrocarbyl group having 2 to 20 carbon atoms or a group comprising said p-valent hydrocarbyl group having an ether linkage (C—O—C) therein and p is an integer from 2 to 6),
of only the glycidyl ether represented by the aforementioned general formula (6) or of this glycidyl ether and an alkylene oxide having 2 to 6 carbon atoms; and
(2) thereafter stopping the polymerization by the addition of an acid.

[27] A method of producing a polyether represented by general formula (4)

$$R^2(\text{—}O\text{—}X_n\text{—}Z_m\text{—}Y)_p \tag{4}$$

{in the formula, $R^2$ is a double bond-terminal p-valent hydrocarbyl group or a group comprising said p-valent hydrocarbyl group having an ether linkage (C—O—C) therein;

n is 1 to 200; m is 0 to 200; 0<n/(n+m)≦1;
Z is an alkyleneoxy group having 2 to 6 carbon atoms;
p is an integer with a value of 2 to 6;
Y is an aliphatically unsaturated bond-free monovalent hydrocarbyl group that contains no more than 20 carbon atoms or an aliphatically unsaturated bond-free acyl group that contains no more than 20 carbon atoms;
X is a group represented by the aforementioned general formula (2) or general formula (3); and
the configuration of the X and Z groups may be random, alternating, block, or a combination of the preceding} defined in [12],
wherein the molecular weight distribution (polydispersity) determined versus a polystyrene standard is 1.25 to 1.00, comprising
(1) carrying out a ring-opening polymerization or a ring-opening copolymerization, in the presence of a base catalyst and a p-hydric alcohol with general formula (7)

$R^2(OH)_p$      (7)

(in the formula, $R^2$ is a double bond-terminated p-valent hydrocarbyl group having 2 to 20 carbon atoms or a group comprising said p-valent hydrocarbyl group having an ether linkage (C—O—C) therein and p is an integer from 2 to 6),
of only the glycidyl ether represented by the aforementioned general formula (6) or of this glycidyl ether and an alkylene oxide having 2 to 6 carbon atoms;
(2) replacing the H of a terminal hydroxyl group with an alkali metal by reacting the polymerization product with an alkali metal hydroxide; and
(3) then carrying out a reaction with an aliphatically unsaturated bond-free hydrocarbyl monohalide having no more than 20 carbon atoms, an aliphatically unsaturated bond-free acyl monohalide having no more than 20 carbon atoms, or epichlorohydrin.

[28] A method of producing a polyether represented by general formula (4)

$R^2(—O—X_n—Z_m—Y)_p$      (4)

{in the formula, $R^2$ is an aliphatically unsaturated bond-free p-valent hydrocarbyl group having no more than 20 carbon atoms or a group comprising said p-valent hydrocarbyl group having an ether linkage (C—O—C) therein;
n is 1 to 200; m is 0 to 200; 0<n/(n+m)≦1;
Z is an alkyleneoxy group having 2 to 6 carbon atoms;
p is an integer with a value of 2 to 6;
Y is a double bond-terminated monovalent hydrocarbyl group having 2 to 20 carbon atoms or a double bond-terminated acyl group having 2 to 20 carbon atoms;
X is a group represented by the aforementioned general formula (2) or general formula (3); and
the configuration of the X and Z groups may be random, alternating, block, or a combination of the preceding} defined in [16],
wherein the molecular weight distribution (polydispersity) determined versus a polystyrene standard is 1.25 to 1.00, comprising
(1) carrying out a ring-opening polymerization or a ring-opening copolymerization, in the presence of a base catalyst and a p-hydric alcohol with general formula (7)

$R^2(OH)_p$      (7)

(in the formula, $R^2$ is an aliphatically unsaturated bond-free p-valent hydrocarbyl group having no more than 20 carbon atoms or a group comprising said p-valent hydrocarbyl group having an ether linkage (C—O—C) therein and p is an integer from 2 to 6),
of only the glycidyl ether represented by the aforementioned general formula (6) or of this glycidyl ether and an alkylene oxide having 2 to 6 carbon atoms;
(2) replacing the H of a terminal hydroxyl group with an alkali metal by reacting the polymerization product with an alkali metal hydroxide; and
(3) then carrying out a reaction with a double bond-terminated hydrocarbyl monohalide having 2 to 20 carbon atoms or a double bond-terminated acyl monohalide having 2 to 20 carbon atoms.

[29] The method of producing a polyether according to [22] or [26], wherein the base catalyst is alkali metal hydroxide or alkali metal alcoholate and the acid is an organic acid or an inorganic acid.

[30] The method of producing a polyether according to [23], [24], [25], [27], or [28], wherein the base catalyst is alkali metal hydroxide or alkali metal alcoholate; the alkali metal hydroxide used in step (2) is sodium hydroxide or potassium hydroxide; the hydrocarbyl monohalide is a hydrocarbyl monochloride; and the acyl monohalide is an acyl monochloride.

EFFECTS OF THE INVENTION

The polyethers of claim 1 and particularly claims 2 to 5 as well as their dependent claims are novel polyethers that are straight-chain homopolymers obtained by the ring-opening addition polymerization of a glycidyl ether on a monohydric alcohol or straight-chain copolymers obtained by the ring-opening addition copolymerization of a glycidyl ether and an alkylene oxide on a monohydric alcohol; that have an aliphatically unsaturated bond in a molecular chain terminal group and in particular that have a terminal double bond; and that have a small molecular weight distribution (polydispersity) of 1.25 to 1.00,.

An excellent hydrosilylation reactivity and an excellent radical polymerizability are obtained due to the presence of an aliphatically unsaturated bond in a molecular chain terminal group and particularly due to the presence of a terminal double bond. Because the polyether has the small molecular weight distribution (polydispersity) of 1.25 to 1.00, a particular reaction product or polymer can be very efficiently obtained when the polyether is subjected to a hydrosilylation reaction or radical polymerization.

Moreover, because a substituted alkyleneoxy group is provided by the ring-opening polymerization of the glycidyl ether while a substituted alkyleneoxy group and an alkyleneoxy group are provided by the ring-opening copolymerization of a glycidyl ether and an alkylene oxide, the hydrosilylation reaction product or radical polymerization product may contain a substituted alkyleneoxy group or a substituted alkyleneoxy group and an alkyleneoxy group.

Polyether [9] and particularly polyether [10] exhibits an excellent oxidation resistance while also having the characteristic features cited above.

Polyether 11] and particularly polyethers [12] and [16] polyethers that are straight-chain or branched homopolymers obtained by the ring-opening addition polymerization of a glycidyl ether on a divalent to hexavalent alcohol or straight-chain or branched copolymers obtained by the ring-opening addition polymerization of a glycidyl ether and an alkylene oxide having 2 to 6 carbon atoms on a divalent to hexavalent alcohol; that have an aliphatically unsaturated bond in a molecular chain terminal group or in a linking group and in particular that have a terminal double bond; and that have a small molecular weight distribution (polydispersity) of 1.25 to 1.00.

An excellent hydrosilylation reactivity and an excellent radical polymerizability are obtained due to the presence of an aliphatically unsaturated bond in a molecular chain terminal group and particularly due to the presence of a terminal double bond.

Because the polyether has the small molecular weight distribution (polydispersity) of 1.25 to 1.00, a particular reaction product or polymer can be very efficiently obtained when the polyether is subjected to a hydrosilylation reaction or radical polymerization. Moreover, because a substituted alkyleneoxy group is provided by the ring-opening polymerization of the glycidyl ether while a substituted alkyleneoxy group and an alkyleneoxy group are provided by the ring-opening copolymerization of a glycidyl ether and an alkylene oxide, the hydrosilylation reaction product or radical polymerization product may contain a substituted alkyleneoxy group or a substituted alkyleneoxy group and an alkyleneoxy group.

Polyethers [20] and particularly polyether [21] exhibit an excellent oxidation resistance while also having the characteristic features cited above. Methods of producing polyethers [22] to [28] can produce precisely the above-cited polyethers at good purities.

BEST MODE FOR CARRYING OUT THE INVENTION

The polyether of claim 1 is characteristically represented by general formula (1)

{in the formula, R is a monovalent hydrocarbyl group that contains no more than 20 carbon atoms and that may contain an aliphatically unsaturated bond or is a group comprising said monovalent hydrocarbyl group having an ether linkage (C—O—C) therein;

n is 1 to 200; m is 0 to 200; $0 < n/(n+m) \leq 1$;

Z is an alkyleneoxy group having 2 to 6 carbon atoms;

Y is hydrogen atom or is a group selected from the group consisting of a monovalent hydrocarbyl group that contains no more than 20 carbon atoms and that may contain an aliphatically unsaturated bond, an acyl group that contains no more than 20 carbon atoms and that may contain an aliphatically unsaturated bond, and glycidyl group; and X is a group represented by general formula (2) or general formula (3)

(in the preceding formulas, $R^1$ is a monovalent hydrocarbyl group or monovalent fluorohydrocarbyl group);

wherein the configuration of the X and Z groups may be random, alternating, block, or a combination of the preceding}, wherein either R or Y contains or both R and Y contain an aliphatically unsaturated bond and the molecular weight distribution (polydispersity) determined versus a polystyrene standard is 1.25 to 1.00.

This polyether is a polyglycidyl ether having a main chain comprising only the X groups given by general formulas (2) and (3) or is a glycidyl ether/alkylene oxide copolymer having a main chain comprising both the X groups given by general formulas (2) and (3) and Z groups (alkyleneoxy groups having 2 to 6 carbon atoms).

In either case, a group R (a monovalent hydrocarbyl group that contains no more than 20 carbon atoms and that may contain an aliphatically unsaturated bond or a group comprising said monovalent hydrocarbyl group having an ether linkage (C—O—C) therein) is bonded at one terminal and a group Y (hydrogen atom or a group selected from the group consisting of a monovalent hydrocarbyl group that contains no more than 20 carbon atoms and that may contain an aliphatically unsaturated bond, an acyl group that contains no more than 20 carbon atoms and that may contain an aliphatically unsaturated bond, and glycidyl group) is bonded at the other terminal and either R or Y contains an aliphatically unsaturated bond or both R and Y contain an aliphatically unsaturated bond.

The group X is a divalent organic group derived from a glycidyl ether with general formula (6)

($R^1$ in the formula is a monovalent hydrocarbyl group or monovalent fluorohydrocarbyl group). That is, the group X is a structural unit produced by the ring-opening polymerization of the glycidyl ether with general formula (6). The number n of X groups in a single molecule of the polyether, that is, the average degree of polymerization, is 1 to 200. This average degree of polymerization is preferably 2 to 70 and more preferably is 3 to 55, viewed from the perspective of obtaining an excellent balance among such properties as the capacity to lower the surface tension, permeation capacity, cleansing performance, emulsification capacity, solubilization capacity, and compatibility with various organic solvents and water.

The group Z is an alkyleneoxy group having 2 to 6 carbon atoms and is a divalent organic group derived from an alkylene oxide. Thus, the group Z is a structural unit produced by the ring-opening polymerization of an alkylene oxide having 2 to 6 carbon atoms. The number m of Z groups in a single molecule of the polyether, that is, the average degree of polymerization, is 0 to 200. This average degree of polymerization is preferably 0 to 50 viewed from the perspective of obtaining an excellent balance among such properties as the capacity to lower the surface tension, permeation capacity, cleansing performance, emulsification capacity, solubilization capacity, and compatibility. The case of m=0 corresponds to a polyglycidyl ether, while the case of m=1 to 200 corresponds to a glycidyl ether/alkylene oxide copolymer. However, due to the specification of $0 < n/(n+m) \leq 1$, the group X must be present in each molecule.

n/(n+m) designates the proportion of X groups in the polyether main chain and is greater than 0 but less than or equal to 1. As this value approaches 1, the proportion for the alkyleneoxy group declines and the oxidation resistance improves. Viewed from the perspective of the oxidation resistance, n/(n+m) preferably is greater than 0.5 but less than or equal to 1, that is, $0.5 < n/(n+m) \leq 1$; more preferably is at least 0.9 but less than or equal to 1, that is, $0.9 < n/(n+m) \leq 1$; and most preferably is n/(n+m)=1, that is, m=0. The oxidation resistance is the best at m=0 due to the absence of Z groups.

The configuration of the X and Z groups may be random, alternating, block, or a combination of the preceding. As a consequence, the RO group may also be bonded to a group Z. In addition, the Y group may also be bonded to a group X. The X and Z groups assume a random configuration in the case of a simple ring-opening copolymerization between the glycidyl ether with general formula (6) and an alkylene oxide having 2 to 6 carbon atoms. The product of the polymerization is a block copolymer when ring-opening polymerization is first carried out with the glycidyl ether with general formula (6) followed by ring-opening polymerization with an alkylene oxide having 2 to 6 carbon atoms, or when ring-opening polymerization is first carried out with the alkylene oxide having 2 to 6 carbon atoms followed by ring-opening polymerization with the glycidyl ether with general formula (6). Viewed from the perspective of ease of production, the configuration for the X and Z groups is preferably random followed by block and then a mixture of block and random.

The alkyleneoxy group can be exemplified by ethyleneoxy, propyleneoxy, butyleneoxy, pentyleneoxy, and cyclohexeneoxy. Viewed from the perspective of the capacity to impart hydrophilicity, the ethyleneoxy group is preferred, followed by the propyleneoxy group. A single molecule may also contain a mixture of ethyleneoxy and propyleneoxy groups.

Either R or Y or both R and Y must contain an aliphatically unsaturated bond in each molecule of the polyether with general formula (1), and this aliphatically unsaturated bond is preferably a terminal double bond based on a consideration of the radical polymerizability and hydrosilylation reactivity. Preferred embodiments are the polyether according to claim 2, which is characterized by R being a double bond-terminated monovalent hydrocarbyl group having 2 to 20 carbon atoms or a group comprising said monovalent hydrocarbyl group having an ether linkage (C—O—C) therein and Y being hydrogen atom; the polyether according to claim 3, which is characterized by R being a double bond-terminated monovalent hydrocarbyl group having 2 to 20 carbon atoms or a group comprising said monovalent hydrocarbyl group having an ether linkage (C—O—C) therein and Y being a group selected from the group consisting of an aliphatically unsaturated bond-free monovalent hydrocarbyl group that contains no more than 20 carbon atoms, an aliphatically unsaturated bond-free acyl group that contains no more than 20 carbon atoms, and glycidyl group; the polyether according to claim 4, which is characterized by R being an aliphatically unsaturated bond-free monovalent hydrocarbyl group that contains no more than 20 carbon atoms or a group comprising said monovalent hydrocarbyl group having an ether linkage (C—O—C) therein and Y being a double bond-terminated monovalent hydrocarbyl group having 2 to 20 carbon atoms or a double bond-terminated acyl group having 2 to 20 carbon atoms; and a polyether according to claim 5, which is characterized by R being a double bond-terminated monovalent hydrocarbyl group having 2 to 20 carbon atoms or a group comprising said monovalent hydrocarbyl group having an ether linkage (C—O—C) therein and Y being a double bond-terminated monovalent hydrocarbyl group having 2 to 20 carbon atoms or double bond-terminated acyl group having 2 to 20 carbon atoms.

$R^1$ in the group X in the polyether with general formula (1) and the four polyethers described above is preferably an aliphatically unsaturated bond-free monovalent hydrocarbyl group in order to enable the utilization in an ensuing reaction of only the terminal double bond in R, or only the terminal double bond in Y, or only the terminal double bonds in R and Y. In addition, viewed from the perspective of the oxidation resistance, $0.5 < n/(n+m) \leq 1$ is preferred and $0.9 \leq n/(n+m) \leq 1$ is more preferred. The oxidation resistance is best when m=0 because then n/(n+m)=1 and the Z group is absent.

R in general formula (1) is a monovalent hydrocarbyl group that contains no more than 20 carbon atoms and that may contain an aliphatically unsaturated bond or is a group comprising said monovalent hydrocarbyl group having an ether linkage (C—O—C) therein. Representative examples of R in its embodiment as a monovalent hydrocarbyl group that contains no more than 20 carbon atoms and that may contain an aliphatically unsaturated bond are a double bond-terminated monovalent hydrocarbyl group having 2 to 20 carbon atoms and an aliphatically unsaturated bond-free monovalent hydrocarbyl group having no more than 20 carbon atoms. The number of ether linkages in a group comprising said monovalent hydrocarbyl group having an ether linkage (C—O—C) therein is preferably one to three and more preferably is one.

Y is hydrogen atom or is a group selected from the group consisting of monovalent hydrocarbyl group that contains no more than 20 carbon atoms and that may contain an aliphatically unsaturated bond, an acyl group that contains no more than 20 carbon atoms and that may contain an aliphatically unsaturated bond, and glycidyl group. Representative examples of Y in its embodiment as a monovalent hydrocarbyl group that contains no more than 20 carbon atoms and that may contain an aliphatically unsaturated bond are a double bond-terminated monovalent hydrocarbyl group having 2 to 20 carbon atoms and an aliphatically unsaturated bond-free monovalent hydrocarbyl group having no more than 20 carbon atoms. Representative examples of Y in its embodiment as an acyl group that contains no more than 20 carbon atoms and that may contain an aliphatically unsaturated bond are a double bond-terminated acyl group having 2 to 20 carbon atoms and aliphatically unsaturated bond-free acyl group having no more than 20 carbon atoms.

In the present invention, "terminal double bond" and "double bond-terminated" refer to the double bond in $CH_2=CH—$ and $CH_2=C(CH_3)—$. The double bond-terminated monovalent hydrocarbyl group having 2 to 20 carbon atoms constituting R or Y can be exemplified by alkenyl, alkenylphenyl, and alkenylaralkyl. The group comprising this monovalent hydrocarbyl group having an ether linkage (C—O—C) therein can be exemplified by alkenyloxyalkyl and alkenyloxyphenyl. The aliphatically unsaturated bond-free monovalent hydrocarbyl group having no more than 20 carbon atoms constituting R or Y can be exemplified by alkyl, phenyl, alkylphenyl, aralkyl, and alkylaralkyl. The group comprising this monovalent hydrocarbyl group having an ether linkage (C—O—C) therein can be exemplified by alkyloxyalkyl and alkyloxyphenyl.

The alkenyl encompassed by R and Y as cited above can be exemplified by vinyl, allyl, methallyl, 3-butenyl, 1,1-dimethyl-2-propenyl, i.e., the group represented by the formula

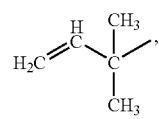

4-pentenyl, 5-hexenyl, 10-undecenyl, and isoprenyl. The alkenylphenyl encompassed by R and Y as cited above can be exemplified vinylphenyl and allylphenyl. The alkenylaralkyl encompassed by R and Y as cited above can be exemplified by vinylbenzyl and allylbenzyl. The alkenyloxyalkyl encompassed by R and Y as cited above can be exemplified by vinyloxyethyl, allyloxyethyl, butenoxyethyl, pentenyloxyethyl, hexenyloxyethyl, allyloxypropyl. The alkenyloxyphenyl encompassed by R and Y as cited above can be exemplified by vinyloxyphenyl and allyloxyphenyl.

The alkyl encompassed by R and Y as cited above can be exemplified by methyl, ethyl, propyl, butyl, pentyl, hexyl, and an alkyl having 7 to 20 carbon atoms. The alkylphenyl encompassed by R and Y as cited above can be exemplified by tolyl, xylyl, ethylphenyl, propylphenyl, and octylphenyl. The alkylaralkyl encompassed by R and Y as cited above can be exemplified by tolylmethyl. The alkyloxyalkyl (i.e., alkoxyalkyl) encompassed by R as cited above can be exemplified by methoxyethyl, ethoxyethyl, propoxyethyl, methoxypropyl, ethoxypropyl, and propoxypropyl. The alkyloxyphenyl (i.e., alkoxyphenyl) encompassed by R as cited above can be exemplified by methoxyphenyl, ethoxyphenyl, and propoxyphenyl.

The group having 2 to 20 carbon atoms constituting Y can be exemplified by acryl, methacryl, crotonyl, and undecenoyl. The aliphatically unsaturated bond-free acyl group having no more than 20 carbon atoms constituting Y can be exemplified by acetyl, propionyl, butanoyl, pentanoyl, hexanoyl, heptanoyl, octanoyl, decanoyl, dodecanoyl, tridecanoyl tetradecanoyl, hexadecanoyl, octadecanoyl, and palmitoyl.

The $R^1$ in the group X in general formulas (2) and (3) is a monovalent hydrocarbyl group or monovalent fluorohydrocarbyl group. $R^1$ in the group X is preferably an aliphatically unsaturated bond-free monovalent hydrocarbyl group in order to enable the utilization in an ensuing reaction of only the terminal double bond in R, or only the terminal double bond in Y, or only the terminal double bonds in R and Y. The aliphatically unsaturated bond-free monovalent hydrocarbyl group can be exemplified by alkyl, phenyl, alkylphenyl, and aralkyl. The monovalent fluorohydrocarbyl group also preferably lacks an aliphatically unsaturated bond and can be exemplified by perfluoroalkyl. The alkyl can be exemplified by methyl, ethyl, propyl, butyl, pentyl, and hexyl; the alkylphenyl can be exemplified by tolyl and xylyl; and the aralkyl can be exemplified by benzyl. The perfluoroalkyl can be exemplified by trifluoromethyl, pentafluoroethyl, trifluoropropyl, and pentafluorobutyl.

When n is 2 to 200, $—X_n—$ is typically a homopolymer but may be a copolymer. That is, it may be a copolymer comprising a plurality of groups X that have different groups $R^1$ (for example, alkyl and phenyl or methyl and butyl). The copolymer is ordinarily a random copolymer, but may be a block copolymer.

$R^1$ preferably has a small number of carbon atoms in order to impart surface activity to the polyether of claim 1 and the polyethers cited in the preceding embodiments, and an alkyl group having 1 to 4 carbon atoms, and particularly an alkyl group having one carbon atom (i.e., methyl), is preferred. When a plurality of groups $R^1$ is present in one and the same molecule, this is preferably a mixture of alkyl groups having different numbers of carbon atoms (for example, methyl and butyl).

The polyether with general formula (1) according to claim 1 has a molecular weight distribution (polydispersity) determined versus a polystyrene standard of 1.25 to 1, and preferably 1.10 to 1.00. The molecular weight distribution (polydispersity) determined versus a polystyrene standard can be determined by the method described in Examples. Polyether having this small molecular weight distribution (polydispercity) can be readily produced by the preparative methods described below.

The group R in the polyether according to claim 2 is a double bond-terminated monovalent hydrocarbyl group having 2 to 20 carbon atoms or is a group comprising this a monovalent hydrocarbyl group having an ether linkage (C—O—C) therein, and this terminal double bond is highly reactive. This polyether, because it has a hydrophobic group R at one terminal and because the Y at the other terminal is hydrogen atom, thus bears hydroxyl group at the other terminal and therefore exhibits an excellent surface activity. In particular, an excellent surface activity is exhibited when R is double bond-terminated monovalent hydrocarbyl group having 2 to 20 carbon atoms, $R^1$ is an alkyl group having 1 to 4 carbon atoms and particularly methyl, and the group Z is either not present or, if present, is ethyleneoxy, propyleneoxy or ethyleneoxy+propyleneoxy. Among the preceding possibilities, an excellent oxidation resistance is also exhibited when little group Z is present (i.e., $0.9 \leq n/(n+m) \leq 1$ is satisfied) and in particular when the group Z is absent (m=0). Thus, the polyether according to claim 2 is useful as a nonionic surfactant, as a reactive surfactant for emulsion polymerization, and as an intermediate in the production of polyether-modified organopolysiloxanes using the hydrosilylation reaction.

An anionic reactive surfactant can be synthesized by modification of the hydroxyl group at the other terminal. For example, the ammonium salt of a sulfate ester can be synthesized by reaction with sulfamic acid. In addition, modification reactions, such as sulfonation, phosphate esterification, carboxymethylation, and so forth, can be carried out according to the methods described on page 7 of JP H03-503168 A. The reactive surfactant produced in this manner can be used as an emulsifying agent for emulsion polymerization, as a modifier for polymers, and as an intermediate in the production of polyether-modified organopolysiloxanes using the hydrosilylation reaction.

In the case of the polyether according to claim 3, R has a terminal double bond, which is highly reactive, and the Y at the other terminal does not have an aliphatically unsaturated bond. This polyether is therefore useful as a starting material for copolymerization with another vinyl monomer and as an intermediate for the preparation of polyether-modified organopolysiloxanes using the hydrosilylation reaction. When the Y in this polyether is glycidyl group, the high reactivity makes this polyether useful as a modifier for polymers and resins.

In the case of the polyether according to claim 4, the group R does not contain an aliphatically unsaturated bond and the Y at the other terminal has a terminal double bond. Due to the high reactivity of this terminal double bond, this polyether is useful as a starting material for copolymerization with another vinyl monomer, as a starting material for the preparation of polyether-modified organopolysiloxanes using the hydrosilylation reaction, and as a base component of crosslinkable compositions.

In the case of the polyether according to claim 5, the group R has a terminal double bond and the group Y also has a terminal double bond, making this polyether useful as a starting material for the preparation of block copolymers and as a base component of crosslinkable compositions.

The method of producing a polyether according to polyether [22] will now be described. Among polyethers represented by general formula (1), the polyether according to claim 2—in which R is a double bond-terminated monovalent hydrocarbyl group having 2 to 20 carbon atoms or a group comprising said monovalent hydrocarbyl group having an ether linkage (C—O—C) therein and Y is hydrogen atom—can be readily produced by (1) carrying out a ring-opening polymerization or a ring-opening copolymerization, in the presence of a base catalyst and a monohydric alcohol with general formula (5)

ROH                              (5)

(in the formula, R is a double bond-terminated monovalent hydrocarbyl group having 2 to 20 carbon atoms or a group comprising said monovalent hydrocarbyl group having an ether linkage (C—O—C) therein), of only the glycidyl ether represented by general formula (6) or of this glycidyl ether and an alkylene oxide having 2 to 6 carbon atoms

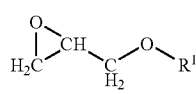
(6)

($R^1$ in the formula is a monovalent hydrocarbyl group or monovalent fluorohydrocarbyl group); and (2) thereafter stopping the polymerization by the addition of an acid.

Among polyethers represented by general formula (1), the polyether according to claim 6—in which R is a double bond-terminated monovalent hydrocarbyl group having 2 to 20 carbon atoms or is a group comprising said monovalent hydrocarbyl group having an ether linkage (C—O—C) therein, $R^1$ in the group X is an aliphatically unsaturated bond-free monovalent hydrocarbyl group, and Y is hydrogen atom—can be readily produced by (1) carrying out a ring-opening polymerization or a ring-opening copolymerization, in the presence of a base catalyst and a monohydric alcohol with general formula (5)

ROH                              (5)

(in the formula, R is a double bond-terminated monovalent hydrocarbyl group having 2 to 20 carbon atoms or a group comprising said monovalent hydrocarbyl group having an ether linkage (C—O—C) therein), of only the glycidyl ether represented by general formula (6) or of this glycidyl ether and an alkylene oxide having 2 to 6 carbon atoms

(6)

($R^1$ in the formula is an aliphatically unsaturated bond-free monovalent hydrocarbyl group); and (2) thereafter stopping the polymerization by the addition of an acid.

The monohydric alcohol represented by general formula (5): ROH (in the formula, R is a double bond-terminated monovalent hydrocarbyl group having 2 to 20 carbon atoms or a group comprising said monovalent hydrocarbyl group having an ether linkage (C—O—C) therein) is the source of the group R in general formula (1). The glycidyl ether with general formula (6) is ring-opening addition polymerized by itself on the hydroxyl group of this monohydric alcohol, or the glycidyl ether with general formula (6) and an alkylene oxide having 2 to 6 carbon atoms are ring-opening addition copolymerized on this hydroxyl group. The groups cited above for the double bond-terminated monovalent hydrocarbyl group having 2 to 20 carbon atoms encompassed by R in general formula (1), and for the group comprising said monovalent hydrocarbyl group having an ether linkage (C—O—C) therein and encompassed by R in general formula (1), are preferred for and cited as examples of the double-bond terminated monovalent hydrocarbyl group having 2 to 20 carbon atoms encompassed by R in general formula (5): ROH as well as the group comprising said monovalent hydrocarbyl group having an ether linkage (C—O—C) therein and encompassed by R in general formula (5): ROH. The monohydric alcohol represented by general formula (5): ROH (in the formula, R is a double bond-terminated monovalent hydrocarbyl group having 2 to 20 carbon atoms or a group comprising said monovalent hydrocarbyl group having an ether linkage (C—O—C) therein) can be exemplified by allyl alcohol, methallyl alcohol, 3-butenyl alcohol, 4-pentenyl alcohol, 5-hexenyl alcohol, 10-undecenyl alcohol, isoprenyl alcohol, ethylene glycol monoallyl ether, propylene glycol monoallyl ether, eugenol, and o-allylphenol. The alkenyl group having 3 to 20 carbon atoms in these alcohols may be branched, while the alkenyl group having 5 to 20 carbon atoms may be cyclic.

The $R^1$ in the glycidyl ether given by general formula (6) is described as in section [0026] and can be exemplified as in section [0026].

The glycidyl ether given by general formula (6) is the source of the group X in general formula (1) and is converted into the group X by the ring-opening polymerization. This glycidyl ether can be exemplified by alkyl glycidyl ethers such as methyl glycidyl ether, ethyl glycidyl ether, propyl glycidyl ether, and butyl glycidyl ether; phenyl glycidyl ether; and perfluoroalkyl glycidyl ethers such as trifluoromethyl glycidyl ether and trifluoropropyl glycidyl ether. A single glycidyl ether or a mixture of two or more glycidyl ethers may be subjected to the polymerization.

Because glycidyl ethers are typically produced by the reaction of epichlorohydrin and an alcohol, they frequently contain unreacted epichlorohydrin and organochlorine compound by-products. Removing the organochlorine compounds by treating the glycidyl ether with a basic alkali metal compound and thereafter purifying by distilling the epoxy compound makes it possible to obtain high-purity polyether with a narrow molecular weight distribution and to reduce the amount of the base catalyst used in the polymerization, and this procedure is therefore preferred.

The alkylene oxide having 2 to 6 carbon atoms is the source of the group Z in general formula (1) and is converted into the group Z by the ring-opening polymerization. The alkylene oxide having 2 to 6 carbon atoms can be exemplified by ethylene oxide, propylene oxide, butylene oxide, pentylene oxide, and hexylene oxide. A single alkylene oxide having 2 to 6 carbon atoms or a mixture of two or more alkylene oxides having 2 to 6 carbon atoms may be subjected to the polymerization.

The glycidyl ether with general formula (6) and the alkylene oxide having 2 to 6 carbon atoms may be submitted to the copolymerization reaction at the molar ratio required in view of the number n and the number m in general formula (1). The best oxidation resistance is obtained when the glycidyl ether with general formula (6) is subjected to ring-opening polymerization by itself to produce a polyglycidyl ether (m=0, i.e., the Z group is absent).

The ring-opening polymerization of the glycidyl ether with general formula (6) is carried out using a base catalyst (also known as a basic catalyst).

The ring-opening copolymerization of the glycidyl ether with general formula (6) with the alkylene oxide having 2 to 6 carbon atoms is carried out using a base catalyst (also known as a basic catalyst).

When a base catalyst is used for the ring-opening polymerization reaction, polymerization goes forward as a living polymerization and provides a polyether ether that contains little reaction by-product and has a small molecular weight distribution (polydispersity) such as 1.25 to 1.00. Usable base catalysts can be exemplified by alkali metal hydroxides such as potassium hydroxide, sodium hydroxide, and so forth; alkali metal alcoholates such as potassium methoxide, potassium ethoxide, potassium t-butoxide, sodium methoxide, sodium ethoxide, and so forth; and various amine compounds, most prominently triethylamine. These catalysts offer advantages from the standpoints of industrial production, reaction rate, the cost of production, and the amount of by-product generation. Among these base catalysts, the alkali metal hydroxides and alkali metal alcoholates are preferred in the present invention, and potassium hydroxide, sodium hydroxide, and potassium t-butoxide are particularly suitable.

A suitable amount of catalyst is 0.005 to 2.0 weight % (as solids) with reference to the total amount of the reaction starting materials (total amount charged) and is more preferably 0.03 to 1.0 weight % (as solids). Depending on the amount of catalyst used, with the alkali metal hydroxide a polyether by-product is produced that is blocked with carbinol groups at both molecular terminals, while with the alkali metal alcoholate a polyether by-product is produced that is blocked with an alkoxy group at one terminal and by an carbinol group at the other molecular terminal. In order to prevent these secondary reactions, in a preferred embodiment the ROH (initiator) is partially alkali-metalated by carrying out a complete reaction between the ROH and alkali metal hydroxide or alkali metal alcoholate, and this is followed by removal of the water or alcohol by-product by a suitable method, for example, distillation by heating under reduced pressure. When potassium t-butoxide is used as the polymerization catalyst, the ring-opening reactivity for the epoxy ring by the potassium t-butoxide per se is very low due to steric hindrance by the t-butyl group. Due to this, a polyether blocked with t-butoxy at one molecular terminal is essentially not produced in a secondary reaction and the ring-opening polymerization proceeds via partially alkali metalated ROH produced by an exchange reaction with the ROH. Accordingly, potassium t-butoxide is preferred for the polymerization catalyst because it enables the production of a high-purity polyether without employing the aforementioned procedure for removing the alcohol or water by-product.

In those instances where the ring-opening polymerization generates a large heat of reaction and reaction control is therefore problematic, the polymerization is preferably carried out in a solvent that is inert with respect to the base catalyst-mediated ring-opening polymerization, such as a hydrocarbon solvent such as toluene, xylene, and so forth, or an ether solvent such as ethylene glycol monomethyl ether, diethylene glycol dimethyl ether, and so forth. Or, while stirring and heating a mixture of the base catalyst and the compound with general formula (5): ROH, the glycidyl ether with general formula (6) is preferably gradually added dropwise, or the glycidyl ether with general formula (6) and the alkylene oxide are each preferably gradually added dropwise in sequence (no particular sequence is specified), or a mixture of the glycidyl ether with general formula (6) and the alkylene oxide is preferably added dropwise.

The preferred polymerization reaction temperature is 50 to 200° C. In a preferred embodiment, the status of the consumption of the starting glycidyl ether with general formula (6) and the starting alkylene oxide having 2 to 6 carbon atoms is monitored, for example, by gas chromatography (GLC), gel permeation chromatography (GPC), nuclear magnetic resonance (NMR), and so forth, while carrying out the ring-opening polymerization at the aforementioned temperature.

A random copolymer may be obtained as follows: by the ring-opening copolymerization of a mixture of one glycidyl ether and one alkylene oxide; by the ring-opening copolymerization of two or more glycidyl ethers and one alkylene oxide; by the ring-opening copolymerization of a mixture of one glycidyl ether and two or more alkylene oxides; or by the ring-opening copolymerization of a mixture of two or more glycidyl ethers and two or more alkylene oxides. A block copolymer is obtained by running the ring-opening polymerization of the glycidyl ether with general formula (6) and, once its consumption has been confirmed, adding the alkylene oxide having 2 to 6 carbon atoms and running its ring-opening polymerization. A block copolymer may also be obtained by running a ring-opening polymerization on the alkylene oxide having 2 to 6 carbon atoms and, once its consumption has been confirmed, adding the glycidyl ether with general formula (6) and running its ring-opening polymerization. —$X_n$— is elaborated as a random copolymer by running ring-opening copolymerization on a mixture of a plurality of glycidyl ethers that have different groups $R^1$ (for example, alkyl and phenyl, methyl and butyl). —$Z_m$— is elaborated as a random copolymer by running ring-opening copolymerization on a mixture of different alkylene oxides. —$X_n$— is obtained as a block copolymer by running a ring-opening polymerization with the glycidyl ether with general formula (6), and, once its consumption has been confirmed, adding a glycidyl ether with general formula (6) that has a different $R^1$ and running the ring-opening polymerization. —$Z_m$— is obtained as a block copolymer by running a ring-opening polymerization with a first alkylene oxide, and, once its consumption has been confirmed, adding a second, different alkylene oxide and running the ring-opening polymerization.

A polyether with general formula (1) (in the formula, R is a double bond-terminated monovalent hydrocarbyl group having 2 to 20 carbon atoms or a group comprising said monovalent hydrocarbyl group having an ether linkage (C—O—C) therein, n is 1 to 200, m is 0 to 200, 0<n/(n+m)≦1, Z is an alkyleneoxy group having 2 to 20 carbon atoms, X is a divalent group represented by the aforementioned general formula (2) or (3) (wherein $R^1$ is a monovalent hydrocarbyl group or monovalent fluorohydrocarbyl group), and Y is hydrogen atom) can be produced by these polymerization reactions when the reaction is stopped by the addition—after confirmation of the consumption of the glycidyl ether with general formula (6) or the glycidyl ether with general formula (6) and the alkylene oxide having 2 to 6 carbon atoms—of organic acid or inorganic acid in the amount necessary to neutralize the base catalyst that has been used. The organic acid can be exemplified by acetic acid, propionic acid, and oxalic acid, while the inorganic acid can be exemplified by hydrochloric acid, sulfuric acid, and phosphoric acid.

The method of producing a polyether according to polyether [23] is described in the following.

The polyether with general formula (1) as specified in claim 3 (in the formula, R is a double bond-terminated monovalent hydrocarbyl group having 2 to 20 carbon atoms or a group comprising said monovalent hydrocarbyl group having an ether linkage (C—O—C) therein, X is a group represented by the aforementioned general formula (2) or (3) (wherein $R^1$ is a monovalent hydrocarbyl group or monovalent fluorohydrocarbyl group), n is 1 to 200, m is 0 to 200, $0<n/(n+m)\leq1$, Z is an alkyleneoxy group having 2 to 6 carbon atoms, and Y is a group selected from the group consisting of an aliphatically unsaturated bond-free monovalent hydrocarbyl group that contains no more than 20 carbon atoms, an aliphatically unsaturated bond-free acyl group that contains no more than 20 carbon atoms, and glycidyl group) can be readily produced by reacting an alkali metal hydroxide with the polyether with general formula (1) obtained by the production method described in section [0034] (in the formula, R is a double bond-terminated monovalent hydrocarbyl group having 2 to 20 carbon atoms or a group comprising said monovalent hydrocarbyl group having an ether linkage (C—O—C) therein, n is 1 to 200, m is 0 to 200, $0<n/(n+m)\leq1$, X is a group represented by the aforementioned general formula (2) or (3) (wherein $R^1$ is a monovalent hydrocarbyl group or monovalent fluorohydrocarbyl group), Z is an alkyleneoxy group having 2 to 6 carbon atoms, and Y is hydrogen atom) in order to replace hydrogen atom constituting Y with an alkali metal and thereafter reacting with an aliphatically unsaturated bond-free hydrocarbyl monohalide having no more than 20 carbon atoms, an aliphatically unsaturated bond-free acyl monohalide having no more than 20 carbon atoms, or epichlorohydrin.

Or, the polyether under consideration can be readily produced by carrying out a ring-opening polymerization or a ring-opening copolymerization, in the presence of a base catalyst and a monohydric alcohol with general formula (5)

$$ROH \quad (5)$$

(in the formula, R is a double bond-terminated monovalent hydrocarbyl group having 2 to 20 carbon atoms or a group comprising said monovalent hydrocarbyl group having an ether linkage (C—O—C) therein), of only the glycidyl ether represented by general formula (6) or of this glycidyl ether and an alkylene oxide having 2 to 6 carbon atoms

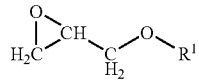 (6)

($R^1$ in the formula is a monovalent hydrocarbyl group or a monovalent fluorohydrocarbyl group); confirming that the glycidyl ether with general formula (6), or the glycidyl ether with general formula (6) and the an alkylene oxide having 2 to 6 carbon atoms, has been consumed and after this confirmation replacing the Y with an alkali metal by reaction with an alkali metal hydroxide; then carrying out a reaction with an aliphatically unsaturated bond-free hydrocarbyl monohalide having no more than 20 carbon atoms, an aliphatically unsaturated bond-free acyl monohalide having no more than 20 carbon atoms, or epichlorohydrin; and removing the alkali metal salt by-product by, for example, filtration, an adsorptive removal method using an adsorbent, and so forth.

Among the polyethers with general formula (1), the polyether according to claim 6—wherein R is a double bond-terminated monovalent hydrocarbyl group having 2 to 20 carbon atoms or a group comprising said monovalent hydrocarbyl group having an ether linkage (C—O—C) therein, $R^1$ in the group X is an aliphatically unsaturated bond-free monovalent hydrocarbyl group, and Y is a group selected from the group consisting of an aliphatically unsaturated bond-free monovalent hydrocarbyl group that contains no more than 20 carbon atoms, aliphatically unsaturated bond-free acyl group that contains no more than 20 carbon atoms, and glycidyl group—can be readily produced by using, for the glycidyl ether with general formula (6) in the preceding production method, a glycidyl ether with general formula (6) in which $R^1$ is an aliphatically unsaturated bond-free monovalent hydrocarbyl group.

The aliphatically unsaturated bond-free hydrocarbyl monohalide having no more than 20 carbon atoms can be exemplified by alkyl chlorides having no more than 20 carbon atoms and alkyl bromides having no more than 20 carbon atoms. Specific examples are propyl chloride, butyl chloride, hexyl chloride, octyl chloride, decyl chloride, phenyl chloride, propyl bromide, butyl bromide, hexyl bromide, octyl bromide, decyl bromide, and phenyl bromide.

The aliphatically unsaturated bond-free acyl monohalide having no more than 20 carbon atoms can be exemplified by saturated aliphatic acid chlorides having no more than 20 carbon atoms and saturated aliphatic acid bromides having no more than 20 carbon atoms. Specific examples are acetyl chloride, propionyl chloride, benzoyl chloride, acetyl bromide, propionyl bromide, and benzoyl bromide.

The method of producing a polyether according to polyether [25] is described in the following.

The polyether with general formula (1) as specified in claim 5 (in the formula, R is a double bond-terminated monovalent hydrocarbyl group having 2 to 20 carbon atoms or is a group comprising said monovalent hydrocarbyl group having an ether linkage (C—O—C) therein, n is 1 to 200, m is 0 to 200, $0<n/(n+m)\leq1$, X is a group represented by the aforementioned general formula (2) or (3), Z is an alkyleneoxy group having 2 to 6 carbon atoms, and Y is a double bond-terminated monovalent hydrocarbyl group having 2 to 20 carbon atoms or an aliphatically unsaturated bond-containing acyl group having 2 to 20 carbon atoms) can be readily produced by reacting an alkali metal hydroxide with the polyether with general formula (1) obtained by the production method described in section (in the formula, R is a double bond-terminated monovalent hydrocarbyl group having 2 to 20 carbon atoms or a group comprising said monovalent hydrocarbyl group having an ether linkage (C—O—C) therein, n is 1 to 200, m is 0 to 200, $0<n/(n+m)\leq1$, X is a group represented by the aforementioned general formula (2) or (3) (wherein $R^1$ is a monovalent hydrocarbyl group or monovalent fluorohydrocarbyl group), Z is an alkyleneoxy group having 2 to 6 carbon atoms, and Y is hydrogen atom) in order to replace hydrogen atom constituting Y with an alkali metal; then carrying out a condensation reaction with a double bond-terminated hydrocarbyl monohalide having 2 to 20 carbon atoms or a double bond-terminated acyl monohalide having 2 to 20 carbon atoms; and removing the alkali metal salt by-product by, for example, filtration, an adsorptive removal method using an adsorbent, and so forth.

Or, the polyether under consideration can be readily produced by carrying out a ring-opening polymerization or a ring-opening copolymerization, in the presence of a base catalyst and a monohydric alcohol with general formula (5)

$$ROH \quad (5)$$

(in the formula, R is a double bond-terminated monovalent hydrocarbyl group having 2 to 20 carbon atoms or a group comprising said monovalent hydrocarbyl group having an ether linkage (C—O—C) therein), of only the glycidyl ether represented by general formula (6) or of this glycidyl ether and an alkylene oxide having 2 to 6 carbon atoms

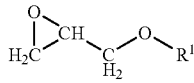 (6)

(R¹ in the formula is a monovalent hydrocarbyl group or monovalent fluorohydrocarbyl group); confirming that the glycidyl ether with general formula (6), or the glycidyl ether with general formula (6) and the alkylene oxide having 2 to 6 carbon atoms, has been consumed and after this confirmation replacing the Y with an alkali metal by reaction with an alkali metal hydroxide; then carrying out a condensation reaction with a double bond-terminated hydrocarbyl monohalide having 2 to 20 carbon atoms or a double bond-terminated acyl monohalide having 2 to 20 carbon atoms; and removing the alkali metal salt by-product by, for example, filtration, an adsorptive removal method using an adsorbent, and so forth.

Among the polyethers with general formula (1), the polyether according to claim 6—wherein R is a double bond-terminated monovalent hydrocarbyl group having 2 to 20 carbon atoms or is a group comprising said monovalent hydrocarbyl group having an ether linkage (C—O—C) therein, R¹ in the group X is aliphatically unsaturated bond-free monovalent hydrocarbyl group, and Y is a aliphatically unsaturated bond-free monovalent hydrocarbyl group that contains no more than 20 carbon atoms, a double bond-terminated acyl group having 2 to 20 carbon atoms, or glycidyl group—can be readily produced by using, for the glycidyl ether with general formula (6) in the preceding production method, glycidyl ether with general formula (6) in which R¹ is an aliphatically unsaturated bond-free monovalent hydrocarbyl group.

The polyether with general formula (1) as specified in claim 4 (in the formula, R is a double bond-terminated monovalent hydrocarbyl group having 2 to 20 carbon atoms or a group comprising said monovalent hydrocarbyl group having an ether linkage (C—O—C) therein, n is 1 to 200, m is 0 to 200, $0 < n/(n+m) \leq 1$, X is a group represented by the aforementioned general formula (2) or (3) (in the formula, R¹ is a monovalent hydrocarbyl group or monovalent fluorohydrocarbyl group), Z is an alkyleneoxy group having 2 to 6 carbon atoms, and Y is an aliphatically unsaturated bond-free monovalent hydrocarbyl group having no more than 20 carbon atoms or an aliphatically unsaturated bond-free acyl group having no more than 20 carbon atoms) can be readily produced by (1) carrying out a ring-opening polymerization or a ring-opening copolymerization, in the presence of a base catalyst and a monohydric alcohol with general formula (5)

ROH    (5)

(in the formula, R is an aliphatically unsaturated bond-free monovalent hydrocarbyl group having no more than 20 carbon atoms or is a group comprising said monovalent hydrocarbyl group having an ether linkage (C—O—C) therein), of only the glycidyl ether represented by the general formula (6) or of this glycidyl ether and an alkylene oxide having 2 to 6 carbon atoms

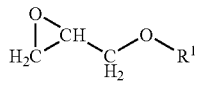 (6)

(R¹ in the formula is a monovalent hydrocarbyl group or monovalent fluorohydrocarbyl group);

(2) replacing hydrogen atom constituting Y with an alkali metal by reacting the polymerization product with an alkali metal hydroxide; and (3) then carrying out a condensation reaction with a double bond-terminated hydrocarbyl monohalide having 2 to 6 carbon atoms or a double bond-terminated acyl monohalide having 2 to 6 carbon atoms and removing the alkali metal salt by-product by, for example, filtration, an adsorptive removal method using an adsorbent, and so forth.

The method of producing a polyether according to polyether [24] is described in the following.

Among the polyethers with general formula (1), the polyether according to claim 6—wherein R is an aliphatically unsaturated bond-free monovalent hydrocarbyl group having no more than 20 carbon atoms or is a group comprising said monovalent hydrocarbyl group having an ether linkage (C—O—C) therein, R¹ in the group X is an aliphatically unsaturated bond-free monovalent hydrocarbyl group, and Y is a double bond-terminated monovalent hydrocarbyl group having 2 to 20 carbon atoms or a double bond-terminated acyl group having 2 to 20 carbon atoms—can be readily produced by using, for the glycidyl ether with general formula (6) in the preceding production method, a glycidyl ether with general formula (6) in which R¹ is an aliphatically unsaturated bond-free monovalent hydrocarbyl group.

The monohydric alcohol represented by general formula (5): ROH (in the formula, R is an aliphatically unsaturated bond-free monovalent hydrocarbyl group having no more than 20 carbon atoms or a group comprising said monovalent hydrocarbyl group having an ether linkage (C—O—C) therein) can be exemplified by methyl alcohol, ethyl alcohol, propyl alcohol, butyl alcohol, pentyl alcohol, hexyl alcohol, alkyl alcohols having 7 to 20 carbon atoms, ethylene glycol monomethyl ether, ethylene glycol monoethyl ether, ethylene glycol monopropyl ether, and ethylene glycol monobutyl ether. The alkyl having 3 to 30 carbon atoms in these alcohols may be branched, while the alkyl having 5 to 20 carbon atoms may be cyclic.

The alkali metal hydroxide used in the preceding reactions can be exemplified by sodium hydroxide and potassium hydroxide.

The double bond-terminated monovalent hydrocarbyl monohalide having 2 to 20 carbon atoms can be exemplified by an alkenyl chloride having 2 to 20 carbon atoms and an alkenyl bromide having 2 to 20 carbon atoms. Specific examples are vinyl chloride, allyl chloride, allyl bromide, and methallyl chloride.

The double bond-terminated acyl monohalide can be exemplified by a double bond-terminated unsaturated aliphatic acid chlorides having 2 to 20 carbon atoms and a double bond-terminated unsaturated aliphatic acid bromides having 2 to 20 carbon atoms. Specific examples are acrylic chloride, methacrylic chloride, crotonic chloride.

Here, a polyether which general formula (1) (wherein R in the formula is a monovalent hydrocarbyl group having 2 to 20 carbon atoms lacking a terminal double bond or is a group comprising said monovalent hydrocarbyl group having an ether linkage (C—O—C) therein, X is a group represented by the aforementioned general formula (2) or (3), n is 1 to 200, m is 0 to 200, 0<n/(n+m)≦1, Z is an alkyleneoxy group having 2 to 6 carbon atoms, and Y is a double bond-terminated monovalent hydrocarbyl group having 2 to 20 carbon atoms or a double bond-terminated acyl group having 2 to 20 carbon atoms) is obtained by converting the other terminal of the molecular chain to the alkali alcoholate by charging alkali metal hydroxide at or in excess of the stoichiometric quantity with respect to the number of moles of hydroxyl in the ROH used and thereafter reacting with double bond-terminated hydrocarbyl monohalide having 2 to 20 carbon atoms, a double bond-terminated acyl monohalide having 2 to 20 carbon atoms, or epichlorohydrin, and removing the alkali metal salt by-product by, for example, filtration, an adsorptive removal method using an adsorbent, and so forth.

All of the starting materials used in the preceding series of production methods are preferably dried to the greatest extent possible by a suitable method. The reason for this is as follows: when water is admixed, it functions as an initiating agent in the polymerization reaction and a polyether in which both terminals are capped by the carbinol group is then produced as a by-product.

The polyether of polyether [1] is represented by general formula (4)

$$R^2(-O-X_n-Z_m-Y)_p \quad (4)$$

{in the formula, $R^2$ is a p-valent hydrocarbyl group that contains no more than 20 carbon atoms and that may contain an aliphatically unsaturated bond or a group comprising said p-valent hydrocarbyl group having an ether linkage (C—O—C) therein; X is a group with the aforementioned general formula (2) or general formula (3); n is 1 to 200; m is 0 to 200; 0<n/(n+m)≦1; Z is an alkyleneoxy group having 2 to 6 carbon atoms; p is an integer with a value of 2 to 6; Y is hydrogen atom or is a group selected from the group consisting of a monovalent hydrocarbyl group that contains no more than 20 carbon atoms and that may contain an aliphatically unsaturated bond, an acyl group that contains no more than 20 carbon atoms and that may contain an aliphatically unsaturated bond, and glycidyl group; and X is a group represented by general formula (2) or general formula (3)

(2)

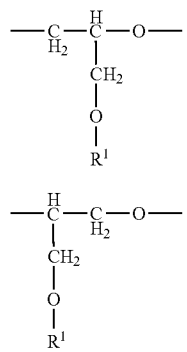

(3)

(in the preceding formulas, $R^1$ is a monovalent hydrocarbyl group or monovalent fluorohydrocarbyl group);
wherein the configuration of the X and Z groups may be random, alternating, block, or a combination of the preceding}, wherein either R or Y contains or both R and Y contain an aliphatically unsaturated bond and the molecular weight distribution (polydispersity) determined versus a polystyrene standard is 1.25 to 1.00.

The difference from the polyether according to claim 1 is that $R^2$ is a p-valent hydrocarbyl group that contains no more than 20 carbon atoms and that may contain an aliphatically unsaturated bond or a group comprising said p-valent hydrocarbyl group having an ether linkage (C—O—C) therein (wherein p is 2 to 6). $R^1$ in the group X is preferably an aliphatically unsaturated bond-free monovalent hydrocarbyl group, and, viewed from the standpoint of the oxidation resistance, n and m preferably satisfy 0.5<n/(n+m)≦1 and more preferably satisfy 0.9<n/(n+m)≦1. The oxidation resistance is the best when m=0 because then n/(n+m)=1 and the group Z is not present. The number of ether linkages in the group comprising the p-valent hydrocarbyl group having an ether linkage (C—O—C) therein is preferably 1 to 3 and more preferably is 1. The definitions, preferred embodiments, and examples of the group X, n, the group Z, m, 0<n/(n+m)≦1, the internal configuration of —$X_n$—, the internal configuration of —$Z_m$—, the configuration of —$X_n$— and —$Z_m$—, and the molecular weight distribution (polydispercity) are as described for the polyether according to claim 1 and its dependent claims.

Among polyethers with general formula (4), the polyether [11] having characteristic features according to claim 12, i.e., $R^2$ is a double bond-terminated divalent to hexavalent hydrocarbyl group having 2 to 20 carbon atoms or a group comprising this divalent to hexavalent hydrocarbyl group having an ether linkage (C—O—C) therein, Y is hydrogen atom, and p is 2 to 6, is a preferred embodiment because it has a terminal double bond and a terminal hydroxyl group. p is 2 in a more preferred embodiment thereamong.

The polyether [11] having characteristic features according to claim 12, i.e., $R^2$ is a double bond-terminated divalent to hexavalent hydrocarbyl group having 2 to 20 carbon atoms or a group comprising this divalent to hexavalent hydrocarbyl group having an ether linkage (C—O—C) therein, Y is an aliphatically unsaturated bond-free monovalent hydrocarbyl group having no more than 20 carbon atoms or an aliphatically unsaturated bond-free acyl group having no more than 20 carbon atoms, and p is 2 to 6, is a preferred embodiment because it has a terminal double bond. p is 2 in a more preferred embodiment thereamong.

Polyether [11] having the characteristic features of polyether [16] i.e., $R^2$ is an aliphatically unsaturated bond-free p-valent hydrocarbyl (i.e., divalent to hexavalent hydrocarbyl) group having no more than 20 carbon atoms or a group comprising this divalent to hexavalent hydrocarbyl group having an ether linkage (C—O—C) therein, Y is a double bond-terminated monovalent hydrocarbyl group having 2 to 20 carbon atoms or a double bond-terminated acyl group having 2 to 20 carbon atoms, and p is 2 to 6, is also a preferred embodiment. p is 2 in a more preferred embodiment thereamong.

The following groups are examples of $R^2$ in its implementation as a double bond-terminated p-valent hydrocarbyl group having 2 to 20 carbon atoms or a group comprising this p-valent hydrocarbyl group having an ether linkage (C—O—C) therein.

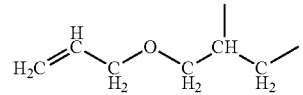

-continued

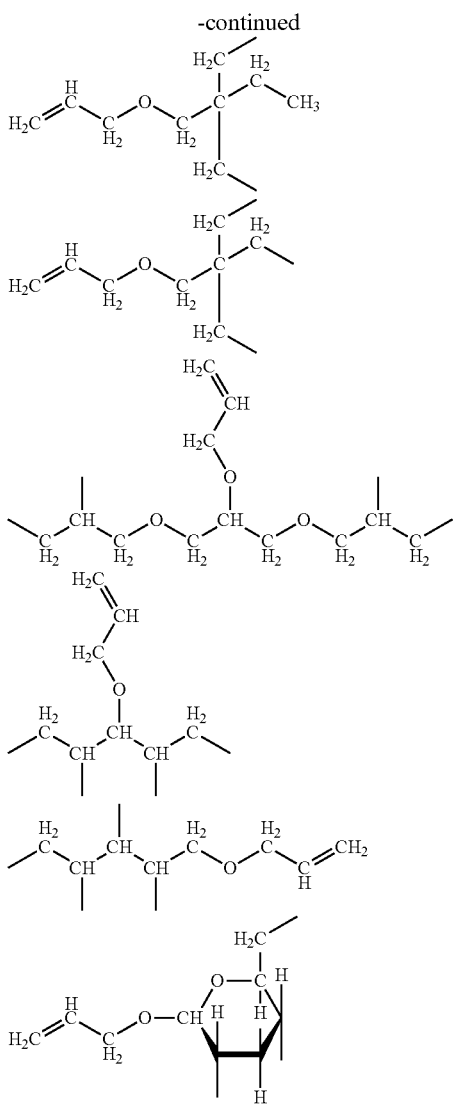

Examples of $R^2$ in its implementation as an aliphatically unsaturated bond-free divalent hydrocarbyl group having no more than 20 carbon atoms are alkylene, phenylene, alkylenephenylene, and alkylenephenylenealkylene. Examples of groups comprising this divalent hydrocarbyl group having an ether linkage (C—O—C) therein are alkyleneoxyalkylene and alkyleneoxyphenylene.

The alkylene can be exemplified by ethylene, propylene, butylene, pentylene, hexylene, heptylene, and octylene. The alkylenephenylene can be exemplified by ethylenephenylene. The alkylenephenylenealkylene can be exemplified by ethylenephenyleneethylene.

$R^1$ in the group X in and their polyethers [12] to [16] and their embodiments is preferably an aliphatically unsaturated bond-free monovalent hydrocarbyl group in order to enable the utilization in an ensuing reaction of only the terminal double bond in $R^2$, or only the terminal double bond in Y, or only the terminal double bonds in $R^2$ and Y. In addition, viewed from the perspective of the oxidation resistance, $0.5<n/(n+m)\leq1$ is preferred and $0.9<n/(n+m)\leq1$ is more preferred. The oxidation resistance is best when m=0 because then n/(n+m)=1 and the Z group is absent.

The definitions, preferred embodiments, and examples of the aliphatically unsaturated-bond-free monovalent hydrocarbyl group encompassed by $R^1$, the aliphatically unsaturated bond-free monovalent hydrocarbyl group having no more than 20 carbon atoms, the aliphatically unsaturated bond-free acyl group having no more than 20 carbon atoms, the double bond-terminated monovalent hydrocarbyl group having 2 to 20 carbon atoms, and the double bond-terminated acyl group having 2 to 20 carbon atoms encompassed by Y, and the molecular weight distribution (polydispercity) determined versus a polystyrene standard being 1.25 to 1.00, have already been provided in the description of the polyether according to claim 1 and its dependent claims.

Among the polyether [12], a polyether in which Y is hydrogen atom exhibits a high reactivity in the terminal double bond in $R^2$, which is a double bond-terminated divalent or hexavalent hydrocarbyl group having 2 to 20 carbon atoms or a group comprising this divalent or hexavalent hydrocarbyl group having an ether linkage (C—O—C) therein. Such polyether has a hydroxyl group at the other terminal since Y is hydrogen atom and thus exhibits an excellent surface activity. Accordingly, it is useful as a nonionic surfactant, as a reactive surfactant for emulsion polymerization, and as an intermediate for the production of polyether-modified organopolysiloxanes through the hydrosilylation reaction.

In addition, an anionic reactive surfactant can be synthesized by modification of this hydroxyl group. For example, an ammonium salt of a sulfate ester can be synthesized by reacting this hydroxyl group with sulfamic acid.

In addition, modification reactions, such as sulfonation, phosphate esterification, carboxymethylation, and so forth, can be carried out at this hydroxyl group according to the methods described on page 7 of JP H03-503168 A. The reactive surfactant produced in this manner is useful as a reactive emulsifying agent for emulsion polymerization, as a modifier for polymers, and as an intermediate in the production of polyether-modified organopolysiloxanes using the hydrosilylation reaction.

Among polyether [12], a polyether in which Y is an aliphatically unsaturated bond-free monovalent hydrocarbyl group having no more than 20 carbon atoms or an aliphatically unsaturated bond-free acyl group having no more than 20 carbon atoms, exhibits a high reactivity in the terminal double bond in $R^2$—which is a double bond-terminated divalent or hexavalent hydrocarbyl group having 2 to 20 carbon atoms or a group comprising this divalent or hexavalent hydrocarbyl group having an ether linkage (C—O—C) therein—and lacks reactivity in Y. It is therefore useful as a monomer for copolymerization with other vinyl monomer and as an intermediate in the production of polyether-modified organopolysiloxanes via the hydrosilylation reaction.

Among polyethers with general formula (4), a polyether in which $R^2$ is a double bond-terminated p-valent hydrocarbyl group having 2 to 20 carbon atoms or this p-valent hydrocarbyl group having an ether linkage (C—O—C) therein and Y is a double bond-terminated monovalent hydrocarbyl group having 2 to 20 carbon atoms or a double bond-terminated acyl group having 2 to 20 carbon atoms, has a terminal double bond in both $R^2$, and Y and this terminal double bond is highly reactive. This polyether is therefore useful as a starting material for the production of block copolymer and as a base component in crosslinkable compositions.

In the polyether according polyether [16], $R^2$, which is a linking group, does not contain an aliphatically unsaturated bond and Y is a double bond-terminated monovalent hydrocarbyl group having 2 to 20 carbon atoms or a double bond-terminated acyl group having 2 to 20 carbon atoms. Thus, it has terminal double bonds at its molecular chain terminals and, because these terminal double bonds are highly reactive, it is useful as a monomer for copolymerization with other vinyl monomer and as an intermediate in the production of polyether-modified organopolysiloxanes via the hydrosilylation reaction.

The method of producing polyether [26] is described in the following.

Polyether [12] with general formula (4) (in the formula, $R^2$ is double bond-terminated p-valent hydrocarbyl group having 2 to 20 carbon atoms or is a group comprising said p-valent hydrocarbyl group having an ether linkage (C—O—C) therein; X is a group represented by the aforementioned general formula (2) or (3); n is 1 to 200; m is 0 to 200; 0<n/(n+m)≦1; Z is an alkyleneoxy group having 2 to 6 carbon atoms; p is an integer with a value of 2 to 6; and Y is hydrogen atom) and having a molecular weight distribution (polydispersity) determined versus a polystyrene standard of 1.25 to 1.00, can be readily produced by (1) carrying out a ring-opening polymerization or a ring-opening copolymerization, in the presence of a base catalyst and a p-hydric alcohol with general formula (7)

$$R^2(OH)_p \quad (7)$$

(in the formula, $R^2$ is a double bond-terminated p-valent hydrocarbyl group having 2 to 20 carbon atoms or a group comprising said p-valent hydrocarbyl group having an ether linkage (C—O—C) therein and p is an integer from 2 to 6), of only the glycidyl ether represented by general formula (6) or of this glycidyl ether and an alkylene oxide having 2 to 6 carbon atoms

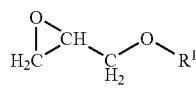

(6)

($R^1$ in the formula is a monovalent hydrocarbyl group or monovalent fluorohydrocarbyl group); and (2) thereafter stopping the polymerization by the addition of an acid.

The method of producing polyether [27] is described in the following.

Polyether [12] with general formula (4) (in the formula, $R^2$ is a double bond-terminated p-valent hydrocarbyl group having 2 to 20 carbon atoms or is a group comprising said p-valent hydrocarbyl group having an ether linkage (C—O—C) therein; X is a group represented by the aforementioned general formula (2) or (3); n is 1 to 200; m is 0 to 200; 0<n/(n+m)≦1; Z is an alkyleneoxy group having 2 to 6 carbon atoms; p is an integer with a value of 2 to 6; and Y is a group selected from the group consisting of an aliphatically unsaturated bond-free monovalent hydrocarbyl group having no more than 20 carbon atoms, an aliphatically unsaturated bond-free acyl group having no more than 20 carbon atoms, and glycidyl group) and having a molecular weight distribution (polydispersity) determined versus a polystyrene standard of 1.25 to 1.00, can be readily produced by reacting an alkali metal hydroxide with polyether with general formula (1) and obtained by the preceding production method (in the formula, $R^2$ is a double bond-terminated p-valent hydrocarbyl group having 2 to 20 carbon atoms or a group comprising said p-valent hydrocarbyl group having an ether linkage (C—O—C) therein, n is 1 to 200, m is 0 to 200, 0<n/(n+m)≦1, Z is a alkyleneoxy group having 2 to 6 carbon atoms, p is an integer with a value of 2 to 6, and Y is hydrogen atom) to replace the Y with an alkali metal; then reacting with an aliphatically unsaturated bond-free hydrocarbyl monohalide having no more than 20 carbon atoms, an aliphatically unsaturated bond-free acyl monohalide having no more than 20 carbon atoms, or epichlorohydrin; and removing the alkali metal salt by-product by a method such as filtration, adsorptive removal with an adsorbent, and so forth.

Or, the polyether under consideration can be readily produced by confirming the consumption of the glycidyl ether with general formula (6) or the glycidyl ether with general formula (6) and the alkylene oxide having 2 to 6 carbon atoms and thereafter replacing the Y with alkali metal by reacting with an alkali metal hydroxide; then reacting with an aliphatically unsaturated bond-free hydrocarbyl monohalide having no more than 20 carbon atoms, an aliphatically unsaturated bond-free acyl monohalide having no more than 20 carbon atoms, or epichlorohydrin; and removing the alkali metal salt by-product by a method such as filtration, adsorptive removal with an adsorbent, and so forth.

The method of producing polyether [28] is described in the following.

Polyether [16] with general formula (4) (in the formula, $R^2$ is an aliphatically unsaturated bond-free p-valent hydrocarbyl group having no more than 20 carbon atoms or a group comprising said p-valent hydrocarbyl group having an ether linkage (C—O—C) therein, X is a group represented by the aforementioned general formula (2) or (3), n is 1 to 200, m is 0 to 200, 0<n/(n+m)≦1, Z is an alkyleneoxy group having 2 to 6 carbon atoms, p is an integer with a value of 2 to 6, and Y is a double bond-terminated monovalent hydrocarbyl group having 2 to 20 carbon atoms or a double bond-terminated acyl group having 2 to 20 carbon atoms) and having a molecular weight distribution (polydispersity) determined versus a polystyrene standard of 1.25 to 1.00, can be readily produced by (1) carrying out a ring-opening polymerization or a ring-opening copolymerization, in the presence of a base catalyst and an aliphatically unsaturated bond-free p-hydric alcohol having no more than 20 carbon atoms and represented by general formula (7)

$$R^2(OH)_p \quad (7)$$

(in the formula, $R^2$ is a p-valent hydrocarbyl group or is a group comprising said p-valent hydrocarbyl group having an ether linkage (C—O—C) therein, and p is an integer from 2 to 6), of only the glycidyl ether represented by general formula (6) or of this glycidyl ether and an alkylene oxide having 2 to 6 carbon atoms

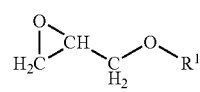

(6)

($R^1$ in the formula is a monovalent hydrocarbyl group or monovalent fluorohydrocarbyl group);

(2) stopping the polymerization by adding an acid;

(3) reacting an alkali metal hydroxide with the polyether with general formula (4) obtained by the preceding production method (in the formula, $R^2$ is an aliphatically unsaturated bond-free p-valent hydrocarbyl group having no more than 20 carbon atoms or a group comprising said monovalent hydrocarbyl group having an ether linkage (C—O—C) therein, n is 1 to 200, m is 0 to 200, 0<n/(n+m)≦1, Z is an alkyleneoxy group having 2 to 6 carbon atoms, p is an integer with a value of 2 to 6, and Y is hydrogen atom) to replace the Y with an alkali metal; and (4) then carrying out a reaction with a double bond-terminated hydrocarbyl monohalide having 2 to 20 carbon atoms or a double bond-terminated acyl monohalide having 2 to 20 carbon atoms and removing the alkali metal salt by-product by a method such as filtration, adsorptive removal with an adsorbent, and so forth.

Or, the polyether under consideration can be readily produced by confirming the consumption of the glycidyl ether with general formula (6) or the glycidyl ether with general formula (6) and an alkylene oxide having 2 to 6 carbon atoms and thereafter replacing the Y with alkali metal by reacting with an alkali metal hydroxide; then reacting with a double bond-terminated hydrocarbyl monohalide having 2 to 20 carbon atoms or a double bond-terminated acyl monohalide having 2 to 20 carbon atoms; and removing the alkali metal salt by-product by a method such as filtration, adsorptive removal with an adsorbent, and so forth.

In the preceding methods of producing polyether [12] (that is, polyether production method [26] and polyether production method [27], the p-hydric alcohol represented by general formula (7): $R^2(OH)_p$ (in the formula, $R^2$ is a double bond-terminated p-valent hydrocarbyl group having 2 to 20 carbon atoms or a group comprising said p-valent hydrocarbyl group having an ether linkage (C—O—C) therein) is the source of the $R^2$ group in general formula (4). The glycidyl ether with general formula (6) is ring-opening addition polymerized by itself on the hydroxyl thereof. Or, the glycidyl ether with general formula (6) and an alkylene oxide having 2 to 6 carbon atoms are ring-opening addition polymerized on the hydroxyl thereof.

In the preceding method of producing a polyether of polyether [16] (that is, the polyether production method), the p-hydric alcohol represented by general formula (7): $R^2(OH)_p$ (in the formula, $R^2$ is an aliphatically unsaturated bond-free p-valent hydrocarbyl group having no more than 20 carbon atoms or a group comprising said p-valent hydrocarbyl group having an ether linkage (C—O—C) therein) is the source of the $R^2$ group in general formula (4). The glycidyl ether with general formula (6) is ring-opening addition polymerized by itself on the hydroxyl thereof. Or, the glycidyl ether with general formula (6) and an alkylene oxide having 2 to 6 carbon atoms are ring-opening addition polymerized on the hydroxyl thereof.

The p-hydric alcohol represented by general formula (7): $R^2(OH)_p$ ($R^2$ is a double bond-terminated p-valent hydrocarbyl group having 2 to 20 carbon atoms or a group comprising said p-valent hydrocarbyl group having an ether linkage (C—O—C) therein) can be a dihydric to hexahydric double bond-terminated unsaturated aliphatic alcohol, or the p-hydric alcohol yielded by alkoxylation of a portion of the hydroxyl in a trihydric to hexahydric double bond-terminated unsaturated aliphatic alcohol, or the p-hydric alcohol yielded by the allyloxylation of a portion of the hydroxyl in a trihydric to hexahydric saturated aliphatic alcohol.

The p-hydric alcohol yielded by the allyloxylation of a portion of the hydroxyl in a dihydric to hexahydric unsaturated aliphatic alcohol can be exemplified by glycerol monoallyl ether, trimethylolpropane monoallyl ether, pentaerythritol monoallyl ether, triglycerol monoallyl ether, xylitol monoallyl ether, and glucose monoallyl ether.

The p-hydric alcohol represented by general formula (7): $R^2(OH)_p$ ($R^2$ is an aliphatically unsaturated bond-free p-valent hydrocarbyl group having no more than 20 carbon atoms or a group comprising said p-valent hydrocarbyl group having an ether linkage (C—O—C) therein) can be exemplified by dihydric to hexahydric saturated aliphatic alcohols, the p-hydric alcohol yielded by alkoxylation of a portion of the hydroxyl in a trihydric to hexahydric saturated aliphatic alcohol, dihydric to tetrahydric phenol, and dihydric to tetrahydric alkylphenol. The dihydric to hexahydric saturated aliphatic alcohol can be exemplified by ethylene glycol, propylene glycol, butylene glycol, glycerol, pentitols such as D-arabitol, and hexitols such as D-sorbitol and D-mannitol.

The other starting materials, the polymerization conditions, the reaction conditions, and so forth in polyether production methods [26], [27] and [28] are the same as already described in the explanation of polyether production methods [22] to [25].

EXAMPLES

The conditions for the GPC analyses and NMR analyses of the samples in Reference Examples and Examples are given below.

[Gel Permeation Chromatography (GPC)]

The gel permeation chromatographic (GPC) instrument was an HLC-8020 gel permeation chromatograph (product of Tosoh Corporation) equipped with a refractive index detector and two TSKgel $GMH_{XL}$-L columns (product of Tosoh Corporation). The sample was submitted to measurement as the 2 weight % chloroform solution. The calibration curve was constructed using standard polystyrenes of known number-average molecular weight and weight-average molecular weight. The number-average molecular weight and the weight-average molecular weight were then determined in terms of the molecular weight of the standard polystyrenes. The polydispersity was calculated from the number-average molecular weight and the weight-average molecular weight.

[$^{13}$C-nuclear Magnetic Resonance ($^{13}$C-NMR) Analysis]

The measurements were carried out using a JNM-EX400 Fourier-transform nuclear magnetic resonance instrument from JEOL Ltd.

The sample was dissolved in deuterochloroform or deuteromethanol and was measured with the addition of tris(acetylacetonato)chromium(III) as relaxation reagent.

Reference Example $^{13}$C-NMR analysis of a commercial methyl glycidyl ether that contained residual starting materials from the synthesis process and organochlorine compound by-products showed that this commercial methyl glycidyl ether contained 3.4 mol % (13700 ppm chlorine) as epichlorohydrin equivalent. 500 g of this methyl glycidyl ether was placed in a four-neck flask equipped with a thermometer, reflux condenser, and stirrer; 25 g of sodium hydroxide powder (average particle diameter≧300 μm) was introduced (this sodium hydroxide powder had been obtained by crushing sodium hydroxide lumps with a hammer); and stirring was carried out for 3 hours at 80° C. under a nitrogen gas. Simple distillation was then carried out at a reduced pressure of 40-50 mmHg to obtain a 360 g of fraction. This fraction was analyzed by NMR and was thereby shown to be methyl glycidyl ether with a purity of 99.9%. Signals associated with the impurities did not appear on the NMR analytical chart. This methyl glycidyl ether fraction was dried by the addition of 5 weight % molecular sieve 4 A to yield a purified methyl glycidyl ether.

Example 1

3.90 g (37.8 mmol) of ethylene glycol monoallyl ether, 0.05 g (0.90 mmol) of potassium hydroxide powder, and 20.0 g (227 mmol) of methyl glycidyl ether purified as in the Reference Example were introduced into a four-neck flask equipped with a thermometer, reflux condenser, and stirrer and were stirred for 2 hours at 120-130° C. under a nitrogen gas. The reaction was cooled to room temperature and the polymerization was stopped by the addition of 0.060 g of acetic acid with stirring. 10 g of toluene was added to the liquid polymerization product; 1 gram of Kyoward 500SN, a hydrotalcite-type adsorbent from Kyowa Chemical Industry Co., Ltd., was then added; and stirring was carried out for 2 hours. The potassium acetate by-product and the adsorbent were removed by filtration and the low boilers were distilled off by heating the filtrate under reduced pressure to obtain 22.7 g (yield=95%) of a clear liquid residue. Analysis of this liquid residue by GPC gave a number-average molecular weight in terms of a standard polystyrene of 940 and a polydispersity of 1.124. NMR analysis of this liquid residue showed it to be poly(methyl glycidyl ether) with average structural formula (8) having an average degree of polymerization of 5.3 (calculated value=6) and the following values for general formula (1): R=allyloxyethyl, $R^1$=methyl, n=5.3, m=0, and Y=hydrogen atom.

Average Structural Formula (8):

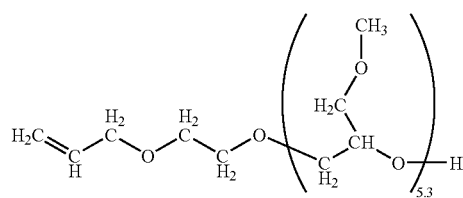

Examples 2 to 5

Liquid poly(methyl glycidyl ether)s having different average degrees of polymerization were prepared by carrying out polymerization and so forth under the same conditions as in Example 1, with the following exceptions: the amount of ethylene glycol monoallyl ether charged was changed from that in Example 1 and potassium t-butoxide was used in place of potassium hydroxide. The values for general formula (1) were as follows: R=allyloxyethyl, $R^1$=methyl, n=average degree of polymerization in Table 1, m=0, and Y=hydrogen atom. The amounts charged and the analytical results are reported in Table 1 below.

TABLE 1

|  | Example 2 | Example 3 | Example 4 | Example 5 |
|---|---|---|---|---|
| ethylene glycol monoallyl ether | 1.86 g 18.2 mmol | 0.93 g 9.1 mmol | 0.46 g 4.5 mmol | 0.46 g 4.5 mmol |
| polymerization catalyst | t-BuOK 0.1 g 0.9 mmol | t-BuOK 0.1 g 0.9 mmol | t-BuOK 0.1 g 0.9 mmol | t-BuOK 0.1 g 0.9 mmol |
| yield | 21.4 g | 20.8 g | 20.5 g | 20.5 G |
| % yield | 98% | 99.5% | 100% | 100% |
| number-average molecular weight | 1638 | 2678 | 4214 | 4139 |
| polydispersity | 1.063 | 1.053 | 1.078 | 1.082 |
| average degree of polymerization (measured value) | 12.3 | 25 | 48 | 46 |
| degree of polymerization (calculated value) | 12.5 | 25 | 50 | 50 |

Example 6

2.20 g (18.9 mmol) of ethylene glycol monobutyl ether, 0.10 g (0.90 mmol) of potassium t-butoxide, and 20.0 g (227 mmol) of methyl glycidyl ether purified as in the Reference Example were introduced into a four-neck flask equipped with a thermometer, reflux condenser, and stirrer and were stirred for 3 hours at 120-130° C. under a nitrogen gas. The reaction was cooled to 80° C. and 0.80 g (20.4 mmol) of sodium hydroxide was added with stirring. Then, while stirring, 2.70 g (22.7 mmol) of allyl bromide was added dropwise, at which time the production of a white precipitate was seen. After stirring for an additional 2 hours at 120° C. and then cooling, 10 g toluene was added and the white precipitate by-product was filtered off. The low boilers were distilled off by heating the filtrate under reduced pressure to obtain 21.5 g of a liquid residue. Analysis of this liquid residue by GPC gave a number-average molecular weight in terms of a standard polystyrene of 1705 and a polydispersity of 1.080. NMR analysis of this liquid residue showed it to be poly(methyl glycidyl ether) with average structural formula (9) having an average degree of polymerization of 12.3 (calculated value=12) and the following values for general formula (1): R=butoxyethyl, $R^1$=methyl, n=12.3, m=0, and Y=allyl.

Average Structural Formula (9):

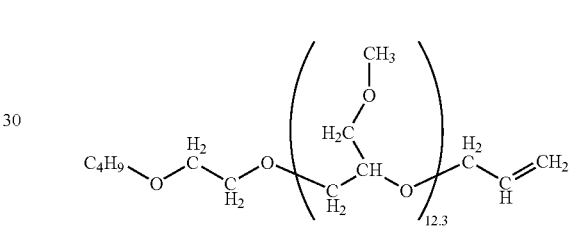

Example 7

31.4 g (yield=99.8%) of a liquid residue was obtained by carrying out polymerization and so forth using the same conditions as in Example 2, with the exception that 29.6 g (227 mmol) of butyl glycidyl ether was used in place of the methyl glycidyl ether used in Example 2. GPC analysis of this liquid residue gave a number-average molecular weight in terms of a standard polystyrene, of 1,967 and a polydispersity of 1.088. NMR analysis of this liquid residue demonstrated that it was a poly(butyl glycidyl ether) with average structural formula (10) having an average degree of polymerization of 12.0 (calculated value=12.5) and the following values for general formula (1): R=allyloxyethyl, $R^1$=butyl, n=12, m=0, and Y=hydrogen atom.

Average Structural Formula (10):

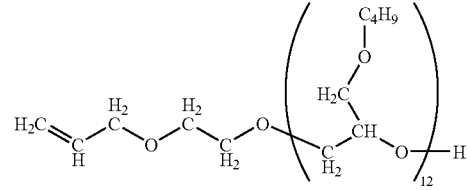

Example 8

26.6 g (yield=100%) of a liquid residue was obtained by carrying out polymerization and so forth using the same conditions as in Example 2, with the exception that a mixture of 14.8 g (113.5 mmol) of butyl glycidyl ether and 10.0 g of methyl glycidyl ether (113.5 mmol) was used in place of the 20.0 g (227 mmol) of methyl glycidyl ether used in Example 2. GPC analysis of this liquid residue gave a number-average molecular weigh in terms of a standard polystyrene of 1,836 and a polydispersity of 1.080. NMR analysis of this liquid residue demonstrated that it was a methyl glycidyl ether.butyl glycidyl ether random copolymer with average structural formula (11) having a total average degree of polymerization of 12.3 (calculated value=12.5, average degree of polymerization of the unit originating from methyl glycidyl ether=6.0, average degree of polymerization of the unit originating from butyl glycidyl ether=6.3) and the following values for general formula (1): R=allyloxyethyl, R¹=butyl+methyl, n=12.3, m=0, and Y=hydrogen atom.

Average Structural Formula (11):

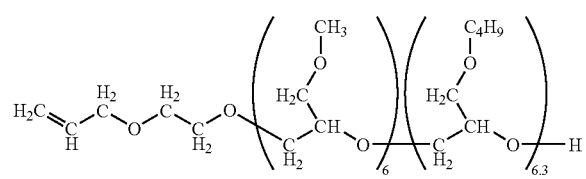

Example 9

25.9 g (yield=97%) of a liquid residue was obtained by carrying out polymerization and so forth using the same conditions as in Example 8, with the exception that after polymerizing the 10.0 g of methyl glycidyl ether (113.6 mmol) by stirring for 2 hours at 120° C., the 14.8 g (113.5 mmol) of butyl glycidyl ether was introduced and stirring was carried out for an additional 2 hours at 120 to 125° C. GPC analysis of this liquid residue gave a number-average molecular weigh in terms of a standard polystyrene of 1,697 and a polydispersity of 1.063. NMR analysis of this liquid residue demonstrated that it was a copolymer (total average degree of polymerization=12.2 (calculated value=12.5)) composed of a poly(butyl glycidyl ether) block with an average degree of polymerization of 6.1 (calculated=6.25) and a poly(methyl glycidyl ether) block with a degree of polymerization of 6.1 (calculated=6.25) and having the following values for general formula (1): R=allyloxyethyl, R¹=methyl+butyl, n=12.2, m=0, and Y=hydrogen atom.

Average Structural Formula (12):

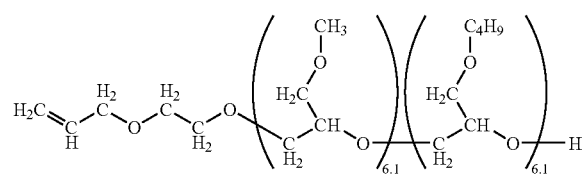

Example 10

A liquid residue was obtained by carrying out polymerization and so forth using the same conditions as in Example 6, with the exception that 1.93 g (18.9 mmol) of ethylene glycol monoallyl ether was used in place of the 2.20 g (18.9 mmol) of ethylene glycol monobutyl ether used in Example 6. GPC analysis of this liquid residue gave a number-average molecular weight in terms of a standard polystyrene, of 1,635 and a polydispersity of 1.061. NMR analysis of this liquid residue demonstrated that it was a poly(methyl glycidyl ether) with average structural formula (13) having an average degree of polymerization of 13.1 (calculated value=12) and the following values for general formula (1): R=allyloxyethyl, R¹=methyl, n=13.1, m=0, and Y=allyl.

Average Structural Formula (13):

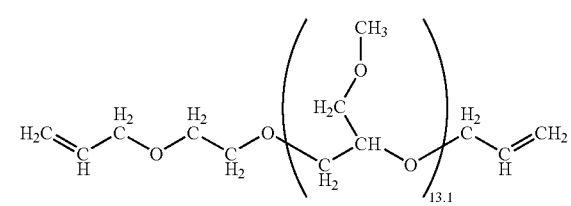

Example 11

2.00 g (18.8 mmol) of diethylene glycol, 0.10 g (0.90 mmol) of potassium t-butoxide, and 20.0 g (227 mmol) of glycidyl methyl ether purified as in the Reference Example were introduced into a four-neck flask equipped with a thermometer, reflux condenser, and stirrer and were stirred for 3 hours at 120-130° C. under a nitrogen gas. After then cooling to 80° C., 1.63 g (40.7 mmol) of sodium hydroxide was introduced with stirring. 5.50 g (45.4 mmol) of allyl bromide was subsequently added dropwise, whereupon the production of a white precipitate was observed. This was followed by stirring for 2 hours at 120° C. and cooling, after which 10 g of toluene was introduced and the white salt by-product was filtered off. The low boilers were distilled from the filtrate by heating under reduced pressure to obtain 21.4 g (yield=91%) of a liquid residue. GPC analysis of this liquid residue gave a number-average molecular weight in terms of a standard polystyrene of 1,778 and a polydispersity of 1.029. NMR analysis of this liquid residue demonstrated that it was a poly(methyl glycidyl ether) with average structural formula (14) that had a total average degree of polymerization of 12.6 (calculated=12) and that had the following values for general formula (4): R²=ethyleneoxyethylene, R¹=methyl, n is greater than 0 and less than 12.6, m=0, p =2, and Y=allyl.

Average Structural Formula (14):

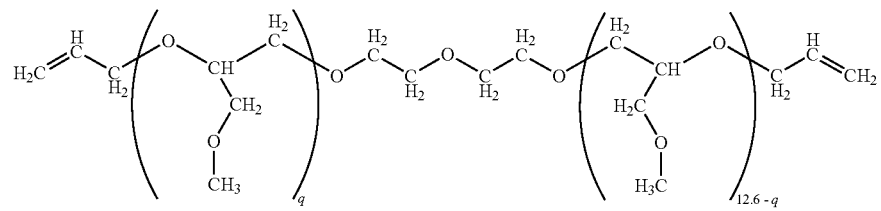

(q in the formula is greater than 0 and less than 12.6)

Example 12

22.3 g (yield=93%) of a liquid residue was obtained by carrying out polymerization and so forth using the same conditions as in Example 11, with the exception that 4.10 g (45.4 mmol) of methallyl chloride was used in place of the allyl bromide used in Example 11. GPC analysis of this liquid residue gave a number-average molecular weight in terms of a standard polystyrene of 2,144 and a polydispersity of 1.040. NMR analysis of this liquid residue demonstrated that it was a poly(methyl glycidyl ether) with average structural formula (15) having a total average degree of polymerization of 12.5 (calculated value=12) and the following values for general formula (4): $R^2$=ethyleneoxyethylene, $R^1$=methyl, n is greater than 0 and less than 12.5, m=0, p=2, and Y=methallyl.

Average Structural Formula (15):

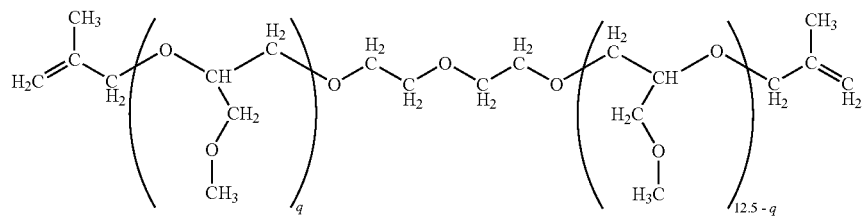

(q in the formula is greater than 0 and less than 12.5)

Example 13

2.40 g (18.2 mmol) of glycerol monoallyl ether, 0.10 g (0.90 mmol) of potassium t-butoxide, and 20.0 g (227 mmol) of methyl glycidyl ether purified as in the Reference Example were introduced into a four-neck flask equipped with a thermometer, reflux condenser, and stirrer and were stirred for 2.5 hours at 120-140° C. under a nitrogen gas. The reaction was cooled to room temperature and the polymerization was stopped by the addition of 0.06 g of acetic acid. 10 g of toluene was then added; Kyoward 500SN, a hydrotalcite-type adsorbent from Kyowa Chemical Industry Co., Ltd., was added; and stirring was carried out for 2 hours. The potassium acetate by-product and the adsorbent were then removed by filtration and the low boilers were distilled off by heating the filtrate under reduced pressure to obtain 22.1 g (yield=99%) of a clear liquid residue. Analysis of this liquid residue by GPC gave a number-average molecular weight in terms of a standard polystyrene of 1,717 and a polydispersity of 1.036. NMR analysis of this liquid residue showed it to be poly (methyl glycidyl ether) with average structural formula (16) that had a total average degree of polymerization of 12.0 (calculated=12.5) and that had the following values for general formula (4): $R^2$=allyloxypropyl, $R^1$=methyl, n is larger than 0 and less than 12, m=0, p=2, and Y=hydrogen atom.

Average Structural Formula (16):

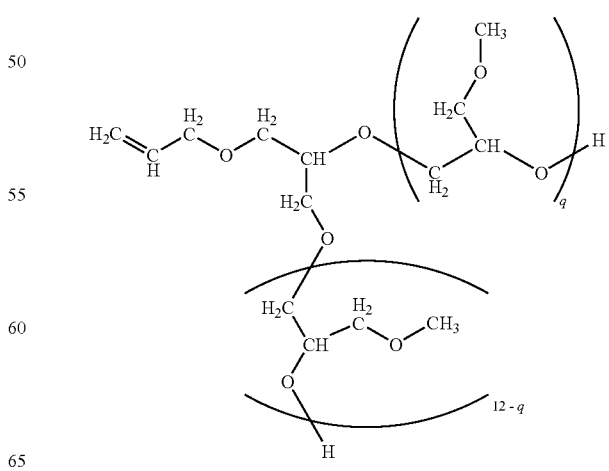

(q in the formula is greater than 0 and less than 12)

Example 14

22.4 g (yield=97%) of a liquid residue was obtained by carrying out polymerization and so forth under the same conditions as in Example 13, with the exception that 3.2 g (18.2 mmol) of pentaerythritol monoallyl ether was used in place of the 2.40 g (18.2 mmol) of glycerol monoallyl ether that was used in Example 13. Analysis of this liquid residue by GPC gave a number-average molecular weight in terms of a standard polystyrene of 2,016 and a polydispersity of 1.072. NMR analysis of this liquid residue showed it to be a poly(methyl glycidyl ether) with average structural formula (17) that had a total average degree of polymerization of 12.0 (calculated=12.5) and the following values in general formula (1): R=allyloxyalkylene, $R^1$=methyl, n is greater than 0 and less than 12, m=0, p=2, and Y=hydrogen atom.

Average Structural Formula (17):

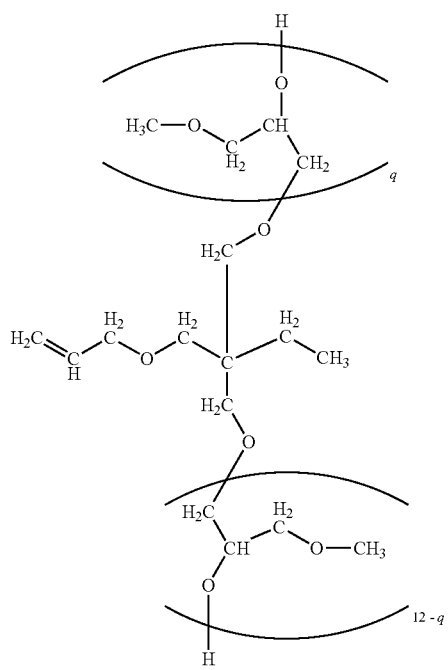

(q in the formula is greater than 0 and less than 12)

Example 15

21.9 g (yield=98%) of a liquid residue was obtained by carrying out polymerization and so forth under the same conditions as in Example 13, with the exception that 2.44 g (18.2 mmol) of o-allylphenol was used in place of the 2.40 g (18.2 mmol) of glycerol monoallyl ether that was used in Example 13. Analysis of this liquid residue by GPC gave a number-average molecular weight in terms of a standard polystyrene of 1,528 and a polydispersity of 1.065. NMR analysis of this liquid residue showed it to be a poly(methyl glycidyl ether) with average structural formula (18) that had an average degree of polymerization of 12.5 (calculated=12.0) and the following values in general formula (1): R=2-allylphenyl, $R^1$=methyl, n=12.5, m=0, and Y=hydrogen atom.

Average Structural Formula (18):

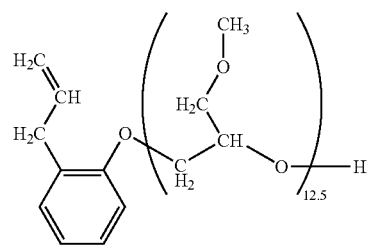

Example 16

22.4 g (yield=97%) of a liquid residue was obtained by carrying out polymerization and so forth under the same conditions as in Example 13, with the exception that 2.98 g (18.2 mmol) of eugenol was used in place of the 2.40 g (18.2 mmol) of glycerol monoallyl ether that was used in Example 13. Analysis of this liquid residue by GPC gave a number-average molecular weight in terms of a standard polystyrene of 1,602 and a polydispersity of 1.049. NMR analysis of this liquid residue showed it to be a poly(methyl glycidyl ether) with average structural formula (19) that had an average degree of polymerization of 12.5 (calculated=12.0) and the following values in general formula (1): R=3-methoxy-4-allylphenyl, $R^1$=methyl, n=12.5, m=0, and Y=hydrogen atom.

Average Structural Formula (19):

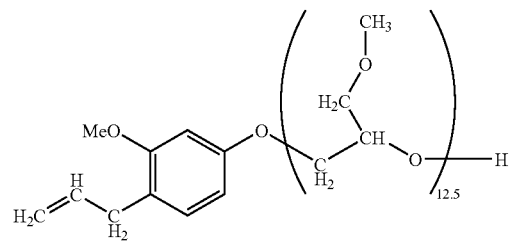

Example 17

20.5 g (yield=96%) of a liquid residue was obtained by carrying out polymerization and so forth under the same conditions as in Example 13, with the exception that 1.31 g (18.2 mmol) of 3-butenol was used in place of the 2.40 g (18.2 mmol) of glycerol monoallyl ether that was used in Example 13. Analysis of this liquid residue by GPC gave a number-average molecular weight in terms of a standard polystyrene of 1,557 and a polydispersity of 1.095. NMR analysis of this liquid residue showed it to be a poly(methyl glycidyl ether) with average structural formula (20) that had an average degree of polymerization of 12.6 (calculated=12.0) and the following values in general formula (1): R=butenyl, $R^1$=methyl, n=12.5, m=0, and Y=hydrogen atom.

Average Structural Formula (20):

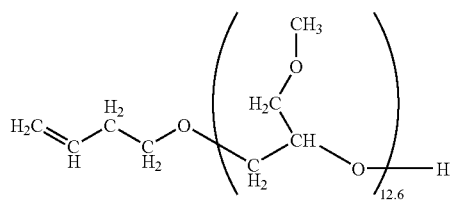

Comparative Example 1

537 g (4.12 moles) of butyl glycidyl ether, 63 g (1.08 moles) of allyl alcohol, and 1.10 g of boron trifluoride etherate were charged to a four-neck flask equipped with a thermometer, reflux condenser, and stirrer and were polymerized by stirring for 26 hours at 35° C. under a nitrogen gas. Workup of the polymerization product as in the examples yielded 552 g (yield=92%) of a liquid residue. This liquid residue had a number-average molecular weight of 521 and a broad polydispersity of 1.410.

Comparative Example 2

A commercially available poly(ethylene oxide) having an average degree of polymerization of 25 and capped at one terminal by the allyl group and at the other terminal by the carbinol group (BL-25T, trade name, from Nikko Chemicals Co., Ltd.) was a solid. In contrast to this, the poly(methyl glycidyl ether) produced in Example 17, which had an average degree of polymerization of 12.6 (in general formula (1): R=butenyl, $R^1$=methyl, n=12.6, m=0, and Y=hydrogen atom), was a liquid despite having about the same molecular weight.

INDUSTRIAL APPLICABILITY

The polyether of the present invention with general formula (1) and the polyether of the present invention with general formula (4) are useful as intermediates in the production of polyether-modified organopolysiloxanes using the hydrosilylation reaction, as intermediates for the production of block copolymers, as reactive surfactants for emulsion polymerization, as monomers for copolymerization with other vinyl monomers, as a component of crosslinkable compositions, as a resin modifier, and so forth. They exhibit an excellent performance as an emulsifying agent for various oils and solvents. In particular, they are well suited for use as emulsifying agents and/or dispersants for various mineral oils, various plant oils, aliphatic hydrocarbon-type solvents, alicyclic hydrocarbon-type solvents, aromatic solvents, and various synthetic resins (e.g., various silicones, modified silicones, polyolefins, polyesters, and diene-type polymers such as polybutadiene); they are also useful as emulsifying agents and solubilizers for essential oils and fragrances.

The polyether with general formula (1) or (4) in which R or $R^2$ is double bond-terminated monovalent hydrocarbyl group having 2 to 20 carbon atoms or a group comprising said monovalent hydrocarbyl group having an ether linkage (C—O—C) therein and Y is hydrogen atom is useful as an intermediate for the production of polyether-modified organopolysiloxanes using the hydrosilylation reaction, as a reactive surfactant for emulsion polymerization, and as a monomer for copolymerization with other vinyl monomers.

The polyether with general formula (1) or (4) in which R or $R^2$ is double bond-terminated monovalent hydrocarbyl group having 2 to 20 carbon atoms or a group comprising said monovalent hydrocarbyl group having an ether linkage (C—O—C) therein and Y is a terminal double bond-free monovalent hydrocarbyl group having 2 to 20 carbon atoms or a terminal double bond-free acyl group having 2 to 20 carbon atoms is useful as monomer for copolymerization with other vinyl monomers and as an intermediate for the production of polyether-modified organopolysiloxanes using the hydrosilylation reaction.

The polyether with general formula (1) or (4) in which R or $R^2$ is a terminal double bond-free monovalent hydrocarbyl group having 2 to 20 carbon atoms or a group comprising said monovalent hydrocarbyl group having an ether linkage (C—O—C) therein and Y is a double bond-terminated monovalent hydrocarbyl group having 2 to 20 carbon atoms or a double bond-terminated acyl group having 2 to 20 carbon atoms is useful as monomer for copolymerization with other vinyl monomers and as an intermediate for the production of polyether-modified organopolysiloxanes using the hydrosilylation reaction.

The polyether with general formula (1) or (4) in which R or $R^2$ is a double bond-terminated monovalent hydrocarbyl group having 2 to 20 carbon atoms or a group comprising said monovalent hydrocarbyl group having an ether linkage (C—O—C) therein and Y is a double bond-terminated monovalent hydrocarbyl group having 2 to 20 carbon atoms or a double bond-terminated acyl group having 2 to 20 carbon atoms is useful as an intermediate for the production of block copolymers with diorganopolysiloxanes and as monomer for copolymerization with other vinyl monomers.

The method of producing a polyether of the present invention are useful for the production, at high purities and high productivities, of poly(glycidyl ether)s and glycidyl ether.alkylene oxide copolymers that have a terminal double bond at one terminal and the hydroxyl group at the other terminal and that have a molecular weight distribution (polydispersity) determined versus a polystyrene standard of 1.25 to 1.00, poly(glycidyl ether)s and glycidyl ether.alkylene oxide copolymers that have a terminal double bond at one terminal and an aliphatically unsaturated bond-free group at the other terminal and that have a molecular weight distribution (polydispersity) determined versus a polystyrene standard of 1.25 to 1.00, and poly(glycidyl ether)s and glycidyl ether.alkylene oxide copolymers that have a terminal double bond at both terminals and that have a molecular weight distribution (polydispersity) determined versus a polystyrene standard of 1.25 to 1.00.

The invention claimed is:

1. A polyether represented by general formula (1)

{in the formula, R is a double bond-terminated alkenyloxyalkyl group having 2 to 20 carbon atoms, a double bond-terminated alkenyloxyphenyl group having 2 to 20 carbon atoms, or a double bond-terminated allylphenyl group;

n is 1 to 200;

Y is a hydrogen atom or is a group selected from the group consisting of a monovalent hydrocarbyl group that contains no more than 20 carbon atoms and that may contain an aliphatically unsaturated bond, an acyl group that contains no more than 20 carbon atoms and that may contain an aliphatically unsaturated bond, and a glycidyl group; and X is a group represented by general formula (2) or general formula (3)

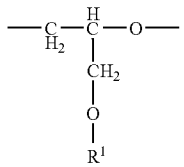
(2)

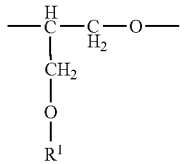
(3)

(in the preceding formulas, $R^1$ is an aliphatically unsaturated bond-free monovalent hydrocarbyl group or monovalent fluorohydrocarbyl group)}, wherein the molecular weight distribution (polydispersity) determined versus a polystyrene standard is 1.25 to 1.00.

2. The polyether according to claim 1, wherein Y is a hydrogen atom.

3. The polyether according to claim 1, wherein Y is a group selected from the group consisting of an aliphatically unsaturated bond-free monovalent hydrocarbyl group that contains no more than 20 carbon atoms, an aliphatically unsaturated bond-free acyl group that contains no more than 20 carbon atoms, and a glycidyl group.

4. The polyether according to claim 1, wherein Y is a double bond-terminated monovalent hydrocarbyl group having 2 to 20 carbon atoms or a double bond-terminated acyl group having 2 to 20 carbon atoms.

5. The polyether according to claim 3, wherein the aliphatically unsaturated bond-free monovalent hydrocarbyl group having no more than 20 carbon atoms constituting Y is a group selected from the group consisting of alkyl, phenyl, alkylphenyl, aralkyl, and alkylaralkyl; the double bond-terminated monovalent hydrocarbyl group having 2 to 20 carbon atoms constituting Y is a group selected from the group consisting of alkenyl, alkenylphenyl, and alkenylaralkyl; and the aliphatically unsaturated bond-free monovalent hydrocarbyl group constituting $R^1$ is a group selected from the group consisting of alkyl, phenyl, and alkylphenyl.

6. The polyether according to claim 5, wherein the double bond-terminated alkenyloxyalkyl group having 2 to 20 carbon atoms constituting R is allyloxyethyl; the double bond-terminated alkenyloxyphenyl group having 2 to 20 carbon atoms constituting R is allyloxyphenyl; the alkyl constituting $R^1$ is a group selected from the group consisting of methyl, ethyl, propyl, and butyl; the alkyl constituting Y is a group selected from the group consisting of methyl, ethyl, propyl, butyl, pentyl, hexyl, and an alkyl having 7 to 20 carbon atoms; the alkenyl constituting Y is a group selected from the group consisting of allyl, methallyl, 3-butenyl, 1,1-dimethyl-2-propenyl, i.e., the group represented by the formula

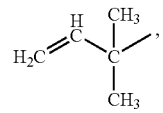

5-hexenyl, 10-undecenyl, and isoprenyl; the double bond-terminated acyl group having 2 to 20 carbon atoms constituting Y is a group selected from the group consisting of acryl, methacryl, crotonyl, and undecenoyl; and the aliphatically unsaturated bond-free acyl group having no more than 20 carbon atoms constituting Y is a group selected from the group consisting of acetyl, propionyl, butanoyl, pentanoyl, hexanoyl, heptanoyl, octanoyl, decanoyl, dodecanoyl, tridecanoyl, tetradecanoyl, hexadecanoyl, and octadecanoyl.

7. The polyether according to claim 4, wherein the aliphatically unsaturated bond-free monovalent hydrocarbyl group having no more than 20 carbon atoms constituting Y is a group selected from the group consisting of alkyl, phenyl, alkylphenyl, aralkyl, and alkylaralkyl; the double bond-terminated monovalent hydrocarbyl group having 2 to 20 carbon atoms constituting Y is a group selected from the group consisting of alkenyl, alkenylphenyl, and alkenylaralkyl; and the aliphatically unsaturated bond-free monovalent hydrocarbyl group constituting $R^1$ is a group selected from the group consisting of alkyl, phenyl, and alkylphenyl.

8. The polyether according to claim 1, wherein n ranges from 2 to 200.

\* \* \* \* \*